(12) United States Patent
Sarazin et al.

(10) Patent No.: US 12,285,627 B2
(45) Date of Patent: Apr. 29, 2025

(54) FABRICATION AND IRRADIATION OF A RADIOACTIVE ISOTOPE SKIN PATCH

(71) Applicants: COLORADO SCHOOL OF MINES, Golden, CO (US); THE REGENTS OF THE UNIVERSITY OF COLORADO, Denver, CO (US)

(72) Inventors: Frédéric Sarazin, Lakewood, CO (US); Jeramy Zimmerman, Golden, CO (US); Rachel Morneau, Los Alamos, NM (US); Martin Ritter, College Park, MD (US); David Westerly, Aurora, CO (US); Quentin Diot, Aurora, CO (US)

(73) Assignees: Colorado School of Mines, Golden, CO (US); The Regents of the University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 16/657,717

(22) Filed: Oct. 18, 2019

(65) Prior Publication Data
US 2020/0188691 A1    Jun. 18, 2020

Related U.S. Application Data

(60) Provisional application No. 62/748,135, filed on Oct. 19, 2018.

(51) Int. Cl.
*A61N 5/10*    (2006.01)
*A61K 51/12*    (2006.01)

(52) U.S. Cl.
CPC ........ *A61N 5/1029* (2013.01); *A61K 51/1279* (2013.01)

(58) Field of Classification Search
CPC .......... A61N 5/1029; A61N 2005/1094; A61N 2005/1096; A61K 51/1279
See application file for complete search history.

(56) References Cited

U.S. PATENT DOCUMENTS 2,517,568 A    8/1950    Hissong
3,488,502 A    1/1970    Dukes
(Continued)

FOREIGN PATENT DOCUMENTS

CZ    293448 B6 *    4/2004
EP    0730872 A1    9/1996
(Continued)

OTHER PUBLICATIONS

Morneau "Development of 166Ho skin patch to treat skin diseases with 1 MW TRIGA reactor." Master's thesis, Colorado School of Mines (Year: 2014).*

(Continued)

*Primary Examiner* — Carrie R Dorna
(74) *Attorney, Agent, or Firm* — Dorsey & Whitney LLP

(57) ABSTRACT

A novel treatment method is disclosed, wherein a patch configured to be placed on a patient's skin is activated, before placement, to deliver localized radiotherapy to a diseased area of the skin. The disclosed devices and methods minimize or prevent collateral damage to the neighboring tissues. In most cases, the disclosed devices and methods include coating a contoured, solid, flexible or conformal substrate with one or more lanthanide elements and then activating (e.g. neutron irradiation) the elements such that its resulting radioisotope emits beta-particles into the diseased skin surface when applied to the patient's skin. Novel processes are described for fabricating and irradiating the lanthanide-based skin patch, for example a holmium-based skin patch.

26 Claims, 21 Drawing Sheets

(56) References Cited

U.S. PATENT DOCUMENTS

| | | | |
|---|---|---|---|
| 3,535,245 | A | 10/1970 | Lindquist et al. |
| 3,539,941 | A | 11/1970 | Halverson |
| 3,584,211 | A | 6/1971 | Rauhut |
| 3,840,015 | A | 10/1974 | Gain |
| 4,323,055 | A | 4/1982 | Kubiatowicz |
| 4,510,924 | A | 4/1985 | Gray |
| 4,763,642 | A | 8/1988 | Horowitz |
| 4,784,116 | A | 11/1988 | Russell et al. |
| 4,891,165 | A | 1/1990 | Suthanthiran |
| 4,946,435 | A | 8/1990 | Suthanthiran et al. |
| 4,994,013 | A | 2/1991 | Suthanthiran et al. |
| 5,266,271 | A | 11/1993 | Bankert et al. |
| 5,405,309 | A | 4/1995 | Carden |
| 5,616,114 | A | 4/1997 | Thornton et al. |
| 5,912,225 | A | 6/1999 | Mao et al. |
| 6,010,445 | A | 1/2000 | Armini et al. |
| 6,059,714 | A | 5/2000 | Armini et al. |
| 6,060,036 | A | 5/2000 | Armini |
| 6,066,856 | A | 5/2000 | Fishman |
| 6,077,213 | A | 6/2000 | Ciezki et al. |
| 6,083,148 | A | 7/2000 | Williams |
| 6,099,457 | A | 8/2000 | Good |
| 6,099,458 | A | 8/2000 | Robertson |
| 6,120,856 | A | 9/2000 | Liberti et al. |
| 6,143,431 | A | 11/2000 | Webster |
| 6,162,165 | A | 12/2000 | Apple et al. |
| 6,163,947 | A | 12/2000 | Coniglione |
| 6,166,184 | A | 12/2000 | Hendriks et al. |
| 6,168,777 | B1 | 1/2001 | Greff et al. |
| 6,183,409 | B1 | 2/2001 | Armini |
| 6,248,057 | B1 | 6/2001 | Mavity et al. |
| 6,264,598 | B1 | 7/2001 | Armini |
| 6,350,226 | B1 | 2/2002 | Fischell et al. |
| 6,400,796 | B1 | 6/2002 | Munro et al. |
| 6,413,245 | B1 | 7/2002 | Yaacobi et al. |
| 6,443,881 | B1 | 9/2002 | Finger |
| 6,527,693 | B2 | 3/2003 | Munro, III et al. |
| 6,749,553 | B2 * | 6/2004 | Brauckman .......... A61N 5/1027 600/3 |
| 7,070,554 | B2 | 7/2006 | White et al. |
| 7,306,559 | B2 | 12/2007 | Williams |
| 7,382,857 | B2 | 6/2008 | Engel |
| 8,231,516 | B2 | 7/2012 | Maschke |
| 8,292,795 | B2 | 10/2012 | Hillstead et al. |
| 8,724,775 | B2 | 5/2014 | Kleinwaechter et al. |
| 9,486,642 | B2 * | 11/2016 | Cipriani ................. A61P 35/00 |
| 9,808,543 | B2 | 11/2017 | Di Pasqua et al. |
| 10,117,578 | B2 | 11/2018 | Finger et al. |
| 11,020,000 | B2 | 6/2021 | Finger et al. |
| 11,865,360 | B2 | 1/2024 | Finger et al. |
| 2003/0233136 | A1 * | 12/2003 | Williams ............. A61N 5/1027 607/117 |
| 2008/0031811 | A1 * | 2/2008 | Ryu ........................ C08J 5/18 424/1.11 |
| 2009/0156881 | A1 | 6/2009 | Stokes |
| 2011/0200704 | A1 | 8/2011 | Rombaut et al. |
| 2013/0317276 | A1 | 11/2013 | D'Andrea |
| 2015/0105602 | A1 | 4/2015 | Finger et al. |
| 2015/0105605 | A1 | 4/2015 | Finger et al. |
| 2015/0182152 | A1 | 7/2015 | Finger et al. |
| 2018/0358142 | A1 | 12/2018 | Vose et al. |
| 2019/0344096 | A1 | 11/2019 | Finger et al. |
| 2020/0188691 | A1 | 6/2020 | Sarazin et al. |
| 2021/0016105 | A1 | 1/2021 | Finger et al. |
| 2022/0266059 | A1 | 8/2022 | Finger et al. |

FOREIGN PATENT DOCUMENTS

| | | | |
|---|---|---|---|
| EP | 0730873 A1 * | 9/1996 | ........... A61N 5/1029 |
| WO | 9844020 A1 | 10/1998 | |
| WO | 9846286 A1 | 10/1998 | |
| WO | 9952565 A1 | 10/1999 | |
| WO | 0019976 A2 | 4/2000 | |
| WO | 2014074712 A2 | 5/2014 | |
| WO | 2015102800 A1 | 7/2015 | |
| WO | 2016038366 A1 | 3/2016 | |
| WO | 2019113192 A1 | 6/2019 | |
| WO | 2022133304 A1 | 6/2022 | |

OTHER PUBLICATIONS

Electron Microscopy Sciences "Kapton Polyimide Film Tape Technical Data Sheets", available online at https://www.emsdiasum.com/microscopy/ technical/datasheet/77708.aspx (Year: 2017).*

Usman et al. "Material science as basis for nuclear medicine: Holmium irradiation for radioisotopes production" AIP Conference Proceedings 1958, 0200020; published online on May 9, 2018; https://doi.org/10.1063/1.5034551 (Year: 2018).*

"Homogeneous" definition retrieved from merriam-webster.com/dictionary/homogeneous on Dec. 20, 2022 (Year: 2022).*

"Evenly" definition retrieved from Google search "define evenly" on Dec. 20, 2022 (Year: 2022).*

Apalla, Zoe et al., "Epidemiological trends in skin cancer", Dermatol Pract Concept, Apr. 30, 2017.

Cho, Eung H. et al., "Radionuclide Therapy for Skin Malignancies", Therapeutic Nuclear Medicine, Medical Radiology, Radiation Oncology, Aug. 14, 2012.

Chung et al., "Treatment of Bowen's disease with a specially designed radioactive skin patch", European Journal of Nuclear Medicine, vol. 27, No. 7, Jul. 2000.

Dupree, Margaret T. et al., "Radiation therapy for Bowen's disease: Lessons for lesions of the lower extremity", J Am Acad Dermatol, Sep. 2001.

Geisse, John K. et al., "Imiquimod 5% cream for the treatment of superficial basal cell carcinoma: A double-blind, randomized, vehicle-controlled study", J Am Acad Dermatol, vol. 47, No. 3, Sep. 2002.

Kim, Joong et al., "β-irradiation ($^{166}$Ho patch)-induced skin injury in mini-pigs: effects on Nf-κB and BOX-2 expression in the skin", Journal of Veterinary Science, 2015.

Klaassen, Nienke et al., "The various therapeutic applications of the medical isotope holium-166: a narrative review", EJNMMI Radiopharmacy and Chemistry, 2009.

Koneru, Bhuvaneswari et al., "Radiotherapeutic bandage for the treatment of squamous cell carcinoma of the skin", Nuclear Medicine and Biology 43, 2016, pp. 333-338.

Lane, Joshua E. et al., "Surgical Margins in the Treatment of Nonmelanoma Skin Cancer and Mohs Micrographic Surgery", Current Surgery, vol. 63, No. 5, Sep. 2005.

Lee, Jong D. et al., "Radionuclide Therapy of Skin Cancers and Bowen's Disease Using a Specially Designed Skin Patch", The Journal of Nuclear Medicine, vol. 38, No. 5,, May 1997.

Nayak, D. et al., "Application of radioisotopes in the field of nuclear medicine", Journal of Radioanalytical and Nuclear Chemistry, vol. 242, No. 2 (1999), 423-432.

Uusijarvi, Helena et al., "Electron- and Positron-Emitting Radiolanthanides for Therapy: Aspects of Dosimetry and Production", The Journal of Nuclear Medicine, vol. 47, No. 5, May 2006.

Andrew , "Vacuum Evaporation and Vacuum Deposition", Handbook of Physical Vapor Deposition (PVD) Processing 2nd Edition, Chapter 6, (2010), Elsevier Inc.

Pai , et al., "TG-69: Radiographic film for megavoltage beam dosimetry", Medical Physics, vol. 34, No. 6, pp. 2228-2258, Jun. 2007.

International Search Report and Written Opinion issued in International Application No. PCT/US2023/085921, mailed on May 13, 2024, 14 pages.

U.S. Appl. No. 63/371,840, filed Aug. 18, 2022, 44 pages.
U.S. Appl. No. 63/520,584, filed Aug. 18, 2023, 48 pages.

* cited by examiner

| Reaction | Activated Isotope | Cross Section |
|---|---|---|
| (n,γ) | $^{166}Ho^m$ | 3.5±0.5 b |
| (n,γ) | $^{166}Ho^g$ | 63±3.3 b |
| (n,γ) | $^{166}Ho^{m+g}$ | 66.5±3.3 b |

FIG. 6
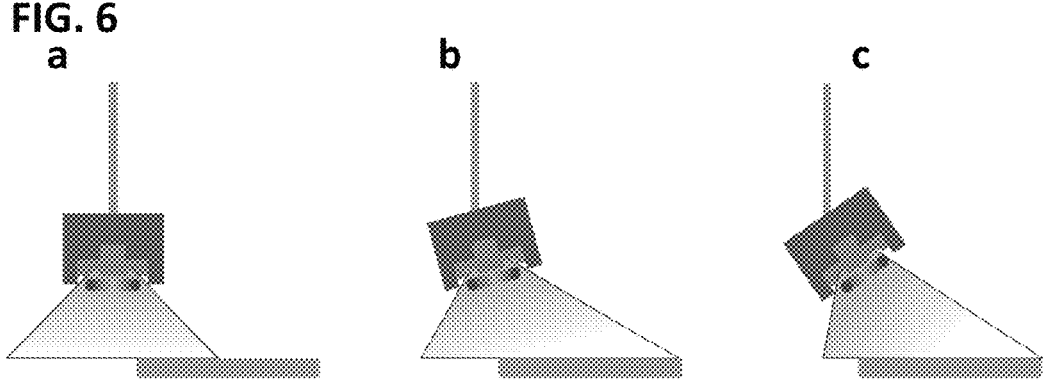
FIG. 7
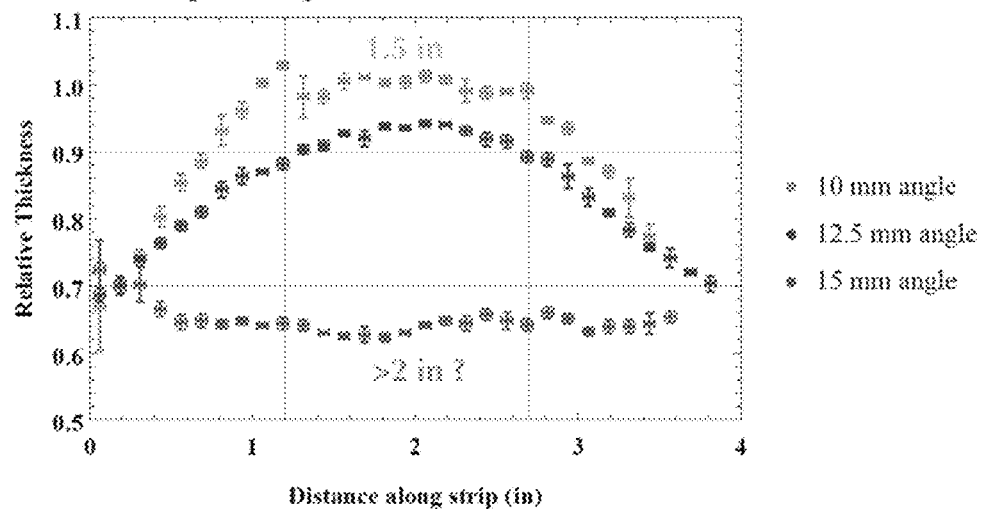
FIG. 8
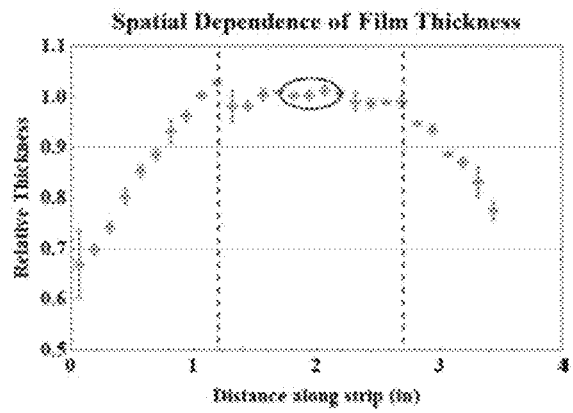
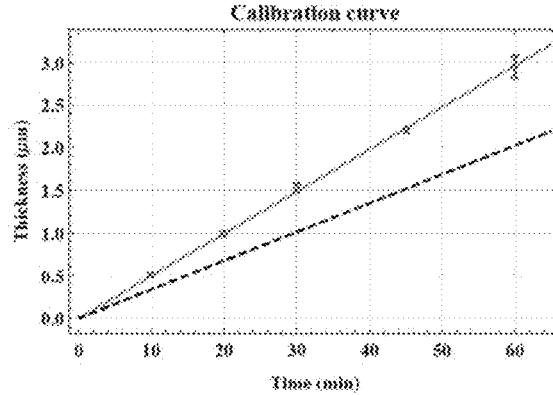

| Run | Predicted (mg) | Mass before (g) | Mass after (g) | Measured (mg) | %Difference |
|---|---|---|---|---|---|
| 1 | 1.67 | 0.13345 | 0.13487 | 1.42± 0.01 | -15.1 |
| 2 | 2.09 | 0.12353 | 0.12515 | 1.62± 0.01 | -22.6 |
| 3 | 1.53 | 0.11436 | 0.11574 | 1.38± 0.01 | -10.0 |
| 4 | 1.39 | 0.10144 | 0.10547 | 1.07± 0.01 | -23.3 |
FIG. 9
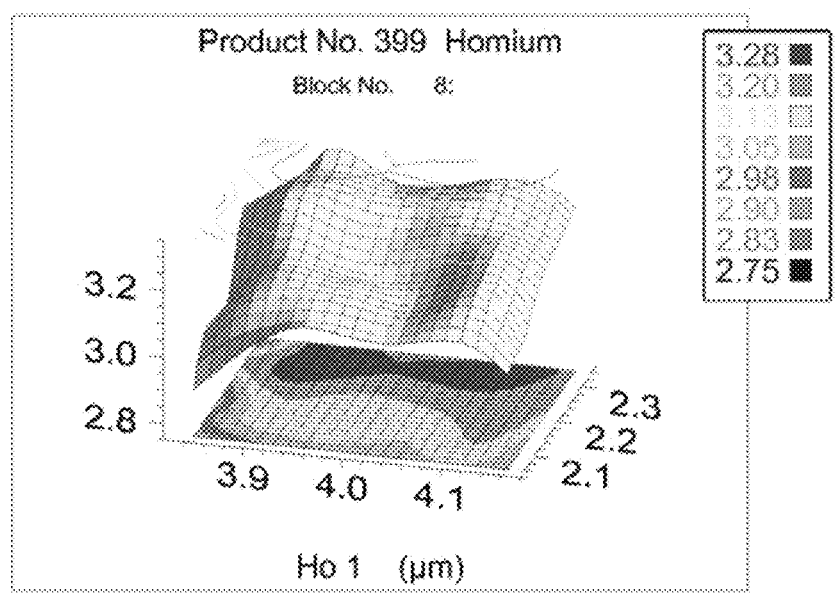
FIG. 10A
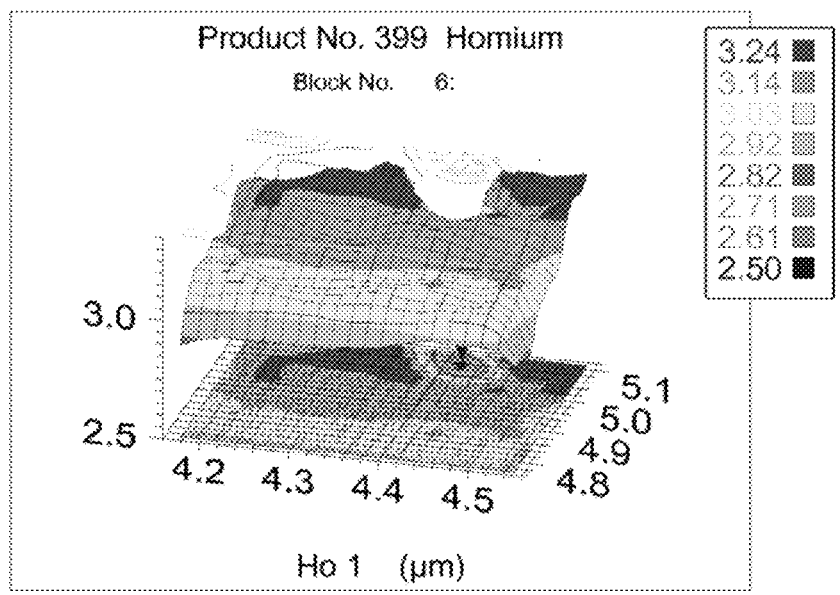
FIG. 10B

| Element | PPM | Isotopes | Neutron Cross Section | Half Life | Decay Mode | Daughter | Half Life | Natural Abundance | Weighted Production |
|---|---|---|---|---|---|---|---|---|---|
| Dysprosium | 30 | Dy-165 | 1.00E+03 | 2.334 h | b- | Ho-165 | Stable | 28.26 | 8.53E+03 |
| Tantalum | 650 | Ta-182 | 1.00E+01 | 114.43 d | b- | W-182 | Stable | 99.988 | 5.92E+03 |
| Lutetium | 20 | Lu-177 | 1.00E+04 | 6.6475 d | b- | Hf-177 | Stable | 2.599 | 4.87E+03 |
| Thulium | 20 | Tm-170 | 5.00E+01 | 128.6 d | b- | Yb-170 | Stable | 100 | 9.76E+02 |
| Samarium | 20 | Sm-153 | 1.00E+02 | 46.284 h | b- | Eu-153 | Stable | 26.74 | 5.81E+02 |
| Nickel | 90 | Ni-59 | 3.00E+00 | 7.6 10^4 y | EC | Co-59 | Stable | 68.077 | 5.23E+02 |
| Copper | 100 | Cu-64 | 2.00E+00 | 12.7 h | b+/b- | Ni-64/Zn-64 | Stable | 69.15 | 3.62E+02 |
| Lanthanum | 40 | La-140 | 6.00E+00 | 1.6781 d | b- | Ce-140 | Stable | 99.911 | 2.85E+02 |
| Ytterbium | 30 | Yb-175 | 3.00E+01 | 4.185 d | b- | Lu-175 | Stable | 31.896 | 2.72E+02 |
| Tungsten | 50 | W-187 | 2.00E+01 | 23.72 h | b- | Re-187 | 41.2 10^9 y | 28.43 | 2.52E+02 |
| Praseodymium | 30 | Pr-142 | 5.00E+00 | 19.12 h | b-/EC | Nd-142/Ce-142 | Stable | 100 | 1.76E+02 |
| Copper | 100 | Cu-66 | 1.20E+00 | 5.12 min | b- | Zn-66 | Stable | 30.85 | 9.12E+01 |
| Samarium | 20 | Sm-151 | 5.00E+01 | 90 y | b- | Eu-151 | 5 10^8 y | 7.37 | 8.11E+01 |
| Aluminum | 130 | Al-28 | 1.00E-01 | 2.24 min | b- | Si-28 | Stable | 100 | 7.94E+01 |
| Iron | 520 | Fe-55 | 1.00E+00 | 2.737 y | EC | Mn-55 | Stable | 5.85 | 5.72E+01 |
| Niobium | 40 | Nb-94 | 8.00E-01 | 20.3 10^3 y | b-/gamma | Mo-94 | Stable | 100 | 5.68E+01 |
| Ytterbium | 30 | Yb-169 | 1.50E+03 | 32.026 d | EC | Tm-169 | Stable | 0.126 | 5.57E+01 |
| Nickel | 90 | Ni-63 | 5.00E+00 | 100 y | b- | Cu-63 | Stable | 3.635 | 4.25E+01 |
| Calcium | 95 | Ca-41 | 1.00E-01 | 1.02 10^5 y | EC | K-41 | Stable | 96.941 | 3.80E+01 |
| Gadolinium | 30 | Gd-153 | 5.00E+02 | 240.4 d | EC | Eu-153 | Stable | 0.2 | 3.26E+01 |
| Samarium | 20 | Sm-155 | 4.00E+00 | 22.3 min | b- | Eu-155 | 4.76 y | 22.71 | 1.95E+01 |
| Yttrium | 10 | Y-90 | 7.00E-01 | 2.7 d | b-/gamma | Zr-90 | Stable | 100 | 1.30E+01 |
| Tungsten | 50 | W-185 | 8.00E-01 | 75.1 d | b- | Re-185 | Stable | 30.64 | 1.10E+01 |
| Gadolinium | 30 | Gd-159 | 1.20E+00 | 18.479 h | b- | Tb-159 | Stable | 24.84 | 9.34E+00 |
| Cerium | 25 | Ce-141 | 3.00E-01 | 32.501 d | b- | Pr-141 | Stable | 88.449 | 7.82E+00 |
| Neodymium | 35 | Nd-147 | 8.00E-01 | 10.98 d | b- | Pm-147 | 2.62 y | 17.2 | 5.44E+00 |

FIG. 16

| Element | PPM | Isotopes | Neutron Cross Section | Half Life | Decay Mode | Daughter | Half Life | Natural Abundance | Weighted Production |
|---|---|---|---|---|---|---|---|---|---|
| Gadolinium | 95 | Gd-161 | 7.00E-01 | 3.646 min | b- | Tb-161 | 6.906 d | 21.86 | 4.73E+00 |
| Calcium | 95 | Ca-45 | 5.00E-01 | 162.67 d | b- | Sc-45 | Stable | 2.086 | 3.72E+00 |
| Ytterbium | 50 | Yb-177 | 1.00E+00 | 1.911 h | b- | Lu-177 | 6.6475 d | 12.887 | 3.62E+00 |
| Neodymium | 35 | Nd-149 | 1.20E+00 | 1.728 h | b- | Pm-149 | 53.08 h | 5.8 | 2.72E+00 |
| Molybdenum | 85 | Mo-99 | 7.00E-02 | 65.94 h | b-/gamma | Tc-99m | 2.11 10^5 y | 24.29 | 2.43E+00 |
| Iron | 220 | Fe-59 | 8.00E-01 | 44.495 d | b- | Co-59 | Stable | 0.28 | 2.04E+00 |
| Cerium | 25 | Ce-143 | 5.00E-01 | 33.039 d | b- | Pr-143 | 13.57 d | 11.114 | 1.61E+00 |
| Molybdenum | 85 | Mo-93 | 5.00E-02 | 4 10^3 y | EC | Nb-93 | Stable | 14.65 | 1.12E+00 |
| Silicon | 130 | Si-31 | 5.00E-02 | 157.3 min | b- | P-31 | Stable | 3.1 | 1.11E+00 |
| Tungsten | 50 | W-181 | 2.00E-01 | 121.2 d | EC | Ta-181 | Stable | 0.12 | 1.10E+00 |
| Neodymium | 55 | Nd-151 | 5.00E-01 | 12.44 min | b- | Sm-150 | Stable | 5.6 | 1.08E+00 |
| Dysprosium | 20 | Dy-159 | 2.00E-01 | 144.4 d | EC | Tb-159 | Stable | 0.095 | 5.95E-01 |
| Samarium | 20 | Sm-145 | 7.00E-01 | 340 d | EC | Pm-145 | 17.7 y | 3.08 | 4.94E-01 |
| Dysprosium | 20 | Dy-157 | 2.00E-01 | 8.14 h | EC | Tb-157 | 71 y | 0.056 | 3.55E-01 |
| Magnesium | 25 | Mg-27 | 2.00E-02 | 9.458 min | b- | Al-27 | Stable | 11 | 3.49E-01 |
| Calcium | 95 | Ca-49 | 5.00E-01 | 8.718 min | b- | Sc-49 | 57.2 min | 0.187 | 2.03E-01 |
| Cerium | 25 | Ce-137 | 4.00E+00 | 9.0 d | b+ | La-137 | 6 10^4 | 0.186 | 2.26E-01 |
| Cerium | 25 | Ce-139 | 5.00E-01 | 137.680 d | EC | La-139 | Stable | 0.251 | 2.75E-02 |
| Carbon | 120 | C-14 | 1.00E-03 | 5730 y | b- | N-14 | Stable | 1.1 | 1.68E-02 |
| Calcium | 95 | Ca-47 | 3.00E-01 | 4.536 d | b- | Sc-47 | 80.38 days | 0.004 | 4.09E-03 |
| Oxygen | 800 | O-19 | 5.00E-05 | 26.464 s | b- | F-19 | Stable | 0.2 | 7.33E-04 |
| Tantalum | 0 | Ta-183 | 2.00E-04 | 5.1 d | b- | W-183 | Stable | 0 | 0 |
| Dysprosium | 0 | Dy-166 | 1.00E-04 | 81.6 h | b- | Ho-166 | 26.763 h | 0 | 0 |
| Lutetium | 0 | Lu-178 | 8.00E-02 | 28.4 min | b- | Hf-178 | Stable | 0 | 0 |
| Samarium | 0 | Sm-146 | 1.50E+02 | 6.8 10^7 y | a | Nd-142 | Stable | 0 | 0 |
| Samarium | 0 | Sm-148 | 3.00E-01 | 7 10^15 y | a | Nd-144 | 2.29 10^15 y | 0 | 0 |

FIG. 16 continued

| Element | PPM | Isotopes | Neutron Cross Section | Half Life | Decay Mode | Daughter | Half Life | Natural Abundance | Weighted Production |
|---|---|---|---|---|---|---|---|---|---|
| Silicon | 0 | Si-32 | 2.00E+01 | 153 y | b- | P-32 | 14.28 d | 0 | 0 |
| Tantalum | 0 | Ta-184 | 1.50E+01 | 8.7 h | b- | W-184 | Stable | 0 | 0 |
| Thulium | 0 | Tm-171 | 1.00E+01 | 1.92 y | b- | Yb-171 | Stable | 0 | 0 |
| Niobium | 0 | Nb-95 | 8.00E+00 | 35 d | b-/gamma | Mo-95 | Stable | 0 | 0 |
| Praseodymium | 0 | Pr-143 | 8.00E+00 | 13.57 d | b- | Nd-143 | Stable | 0 | 0 |
| Samarium | 0 | Sm-147 | 8.00E+00 | 1.06 10^11 y | a | Nd-143 | Stable | 0 | 0 |
| Dysprosium | 0 | Dy-167 | 6.00E+00 | 6.2 min | b- | Ho-167 | 3.1 h | 0 | 0 |
| Cerium | 0 | Ce-144 | 3.00E+00 | 284.893 d | b- | Pr-144 | 17.28 min | 0 | 0 |
| Iron | 0 | Fe-60 | 3.00E+00 | 2.6 10^6 y | b- | Co-60 | 1925 days | 0 | 0 |
| Niobium | 0 | Nb-96 | 3.00E+00 | 24 h | b- | Mo-96 | Stable | 0 | 0 |
| Yttrium | 0 | Y-91 | 1.50E+00 | 58.5 d | b- | Zr-91 | Stable | 0 | 0 |
| Lanthanum | 0 | La-141 | 1.20E+00 | 3.92 h | b-/gamma | Ce-141 | 32.501 days | 0 | 0 |
| Silicon | 0 | Si-33 | 2.00E-01 | 6.18 s | b- | P-33 | 25.3 d | 0 | 0 |
| Magnesium | 0 | Mg-28 | 2.00E-02 | 20.915 h | b- | Al-28 | 2.24 min | 0 | 0 |
| Carbon | 0 | C-15 | 1.00E-07 | 2.449 s | b- | Ne-15 | Stable | 0 | 0 |
| Aluminum | 0 | Al-29 | 0.00E+00 | 6.56 min | b- | Si-29 | Stable | 0 | 0 |
| Aluminum | 0 | Al-30 | 0.00E+00 | 3.60 sec | b- | Si-30 | Stable | 0 | 0 |
| Oxygen | 0 | O-20 | 0.00E+00 | 13.51 s | b- | F-20 | 11.163 s | 0 | 0 |
| Oxygen | 0 | O-21 | 0.00E+00 | 3.42 s | b- | F-21 | 4.158 s | 0 | 0 |
| Samarium | 0 | Sm-156 | 0.00E+00 | 9.4 h | b- | Eu-156 | 15.19 d | 0 | 0 |
| Tantalum | 0 | Ta-185 | 0.00E+00 | 49.4 min | b- | W-185 | 75.1 d | 0 | 0 |
| Tungsten | 0 | W-188 | 0.00E+00 | 69.78 d | b- | Re-188 | 17.004 h | 0 | 0 |
| Copper | 0 | Cu-67 | 0.00E+00 | 61.83 h | b- | Zn-67 | Stable | 0 | 0 |
| Gadolinium | 0 | Gd-162 | 0.00E+00 | 8.4 min | b- | Tb-162 | 7.6 min | 0 | 0 |
| Lanthanum | 0 | La-142 | 0.00E+00 | 91.1 min | b- | Ce-142 | Stable | 0 | 0 |
| Magnesium | 0 | Mg-29 | 0.00E+00 | 1.30 s | b- | Al-29 | 6.56 min | 0 | 0 |

FIG. 16 continued

| Isotope | Decay Mode | Max Energy (keV) | Half-Life |
|---|---|---|---|
| Dy-165 | b- | 453.7 | 2.334 h |
| Lu-177 | b- | 149.35 | 6.6475 d |
| Cu-66 | b- | 1112.1 | 5.12 min |

| Source | Energy (keV) | Half-Life | Activity (Bq) | Energy (keV) | Activity (Bq) |
|---|---|---|---|---|---|
| 109Cd | 88 | 462.6 d | 129 | 79.6+81 | 945 |
| 57Co | 122 | 271.79 d | 18 | 276.4 | 191 |
| 139Ce | 166 | 137.6 d | ≈0 | 302.9 | 488 |
| 203Hg | 279 | 46.61 d | ≈0 | 356.0 | 1651 |
| 113Sn | 392 | 115.1 d | ≈0 | 383.8 | 238 |
| 137Cs | 662 | 30.07 y | 621 | | |
| 88Y | 898 | 106.6 d | ≈0 | | |
| 60Co | 1173 | 5.271 y | 770 | | |
| 60Co | 1332 | 5.271 y | 770 | | |
| 88Y | 1836 | 106.6 d | ≈0 | | |

| Date | Predicted | Experimental (single peak) | Corrected Experimental (double peak) |
|---|---|---|---|
| 06/20 | 4.83± 0.64 μCi | 5.19± 0.26 μCi | 4.33± 0.22 μCi |
| 06/27 | 4.95± 0.32 μCi | 4.61± 0.23 μCi | 3.81± 0.19 μCi |
| 07/05 | 1.84± 0.21 mCi | 1.11± 0.06 mCi | 922± 46.5 μCi |
FIG. 26
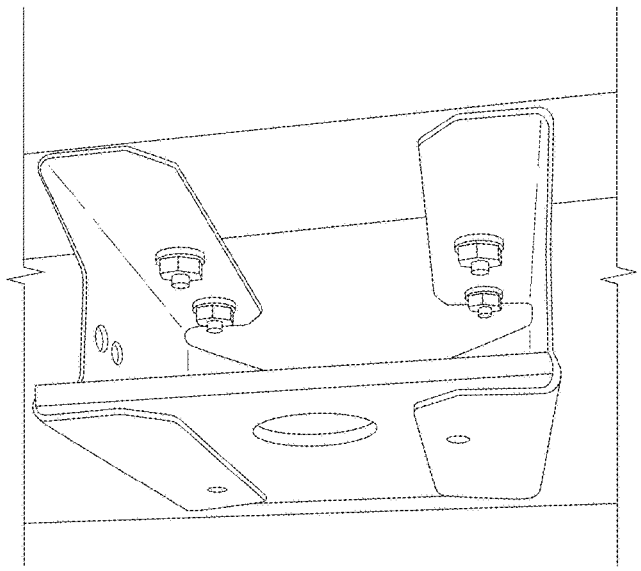
FIG. 27A
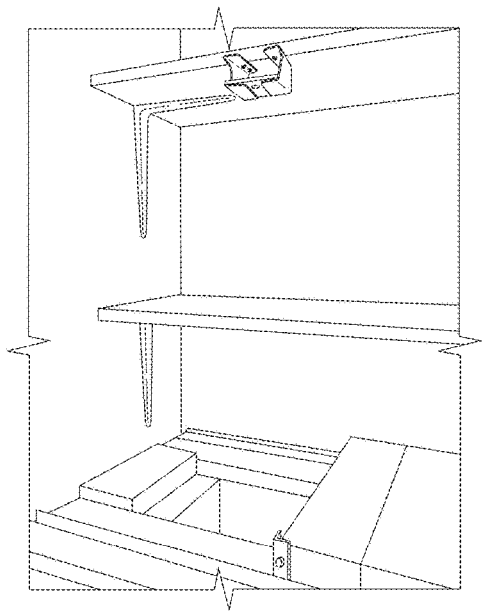
FIG. 27B
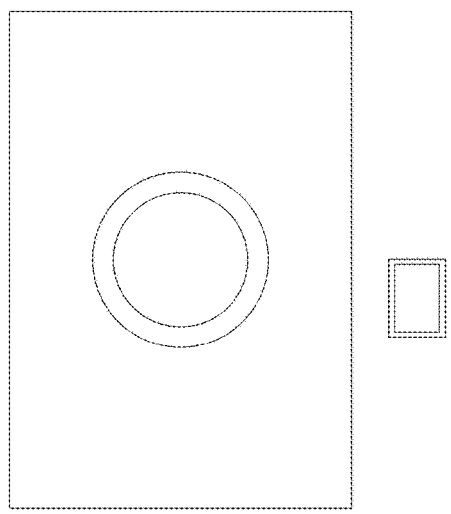
FIG. 28A
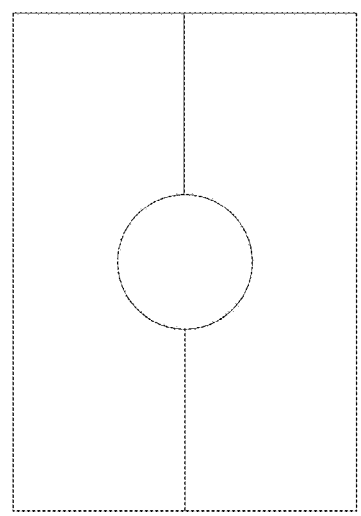
FIG. 28B

| Energy (keV) | Activity | Energy (keV) | Activity |
|---|---|---|---|
| 121.78 | 8183 | 79.6 / 81 | 945 |
| 244.7 | 2170 | 276.4 | 191 |
| 344.28 | 7587 | 302.9 | 488 |
| 411.12 | 639 | 356.0 | 1651 |
| 443.97 | 808 | 383.8 | 238 |
| 778.90 | 3705 | | |
| 867.38 | 1217 | | |
| 964.08 | 4183 | | |
| 1085.87 | 2923 | | |
| 1089.74 | 495 | | |
| 1112.07 | 3905 | | |
| 1212.95 | 406 | | |
| 1299.14 | 464 | | |
| 1408.01 | 6015 | | |

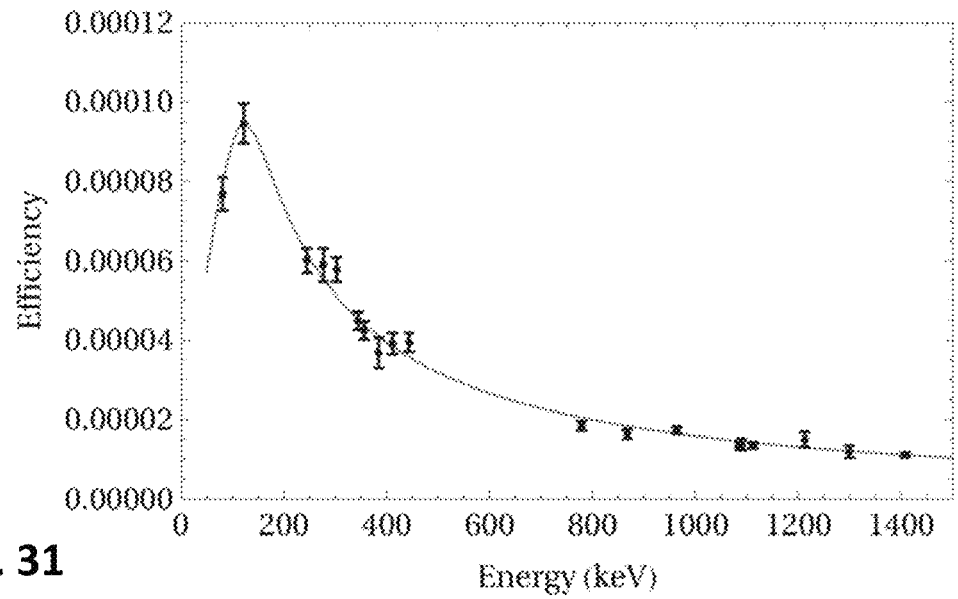
FIG. 31
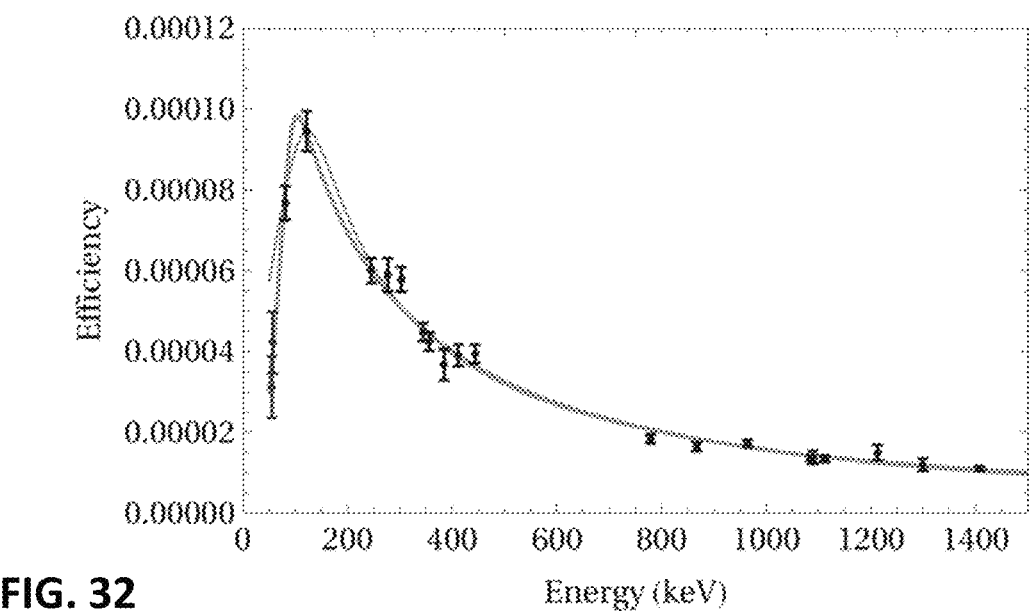
FIG. 32
|  | USGS setup | | Mines setup (after cooling) |
|---|---|---|---|
| Date | Predicted | Measured | |
| 04/05 | 750 ± 35 μCi | 760 ± 42 μCi | |
| 04/18 | 967 ± 35 μCi | 985 ± 54 μCi | 1017 ± 51 μCi |
FIG. 33

FABRICATION AND IRRADIATION OF A RADIOACTIVE ISOTOPE SKIN PATCH

CROSS-REFERENCE TO RELATED APPLICATION

This application claims benefit of priority pursuant to 35 U.S.C. § 119(e) of U.S. provisional patent application No. 62/748,135 entitled "Fabrication And Irradiation Of A Radioactive Isotope Skin Patch," filed on Oct. 19, 2018, which is hereby incorporated by reference in its entirety.

TECHNICAL FIELD

The technology described herein relates generally to devices and methods of using and manufacturing the devices to treat skin cancer. More specifically, disclosed herein are skin patches comprising lanthanide metals that can be activated to create radioactive skin patches for treating various cancers.

BACKGROUND

Skin cancer is the most common form of cancer affecting millions of Americans each year. According to the National Institutes of Health (NIH), approximately 5 million patients are treated each year for skin cancer of all types combined at a cost of $8.1 billion. Since the occurrence rate is highest among elderly people, most of this cost falls on the Social Security Administration's programs, prompting a call to action to prevent skin cancer and to develop cheaper methods to treat it. The vast majority of skin cancer cases are either basal cell carcinoma (BCC) or squamous cell carcinoma (SCC) which are usually non-lethal but can cause disfigurations and infections if not treated appropriately. Age and cumulative sun exposure are the main drivers towards an increased occurrence rate of non-melanoma skin cancers (NMSC) of which BCC and SCC form the vast majority of cases. The prevalence of skin cancer cases places an economic burden on public health services. While decreasing sun exposure (specifically unprotected sun exposure) has some positive benefits in terms of reducing the risk of developing a skin cancer, a large decrease seems unlikely when other health benefits from outdoor activities (and concomitant sun exposure) such as increased vitamin D production and general health seem to outweigh them.

Current treatment options for skin cancer lesions include surgical, cryogenic, chemical, and radiological methods. The most common form of treatment is surgical excision of the lesion. This allows the lesion to be extracted from the body and examined to determine if the tumor has been completely removed from the patient. A less invasive form of surgical treatment is curettage with cautery where the lesion is simply scraped off the patient. This is only applicable for early stages of benign lesions and has a recurrence rate of 10-20% over 5 years. The final surgical method is Mohs' micrographic surgery (MMS), which has a recurrence rate of less than 5%. MMS also usually has good cosmetic results with little to no scaring after the procedure. However, this method is expensive and time consuming. In addition, it is not recommended for large lesions or patients in poor health. Overall, surgical treatment is the easiest and usually cheapest method to remove tumors. Nevertheless, most excisions require skin grafts and are not very well suited for sensitive and cosmetic areas (e.g., nose, lips, eyelids).

Another treatment option involves the use of X-rays to kill the tumor cells. The treatment plans require the deposited X-ray dose to be divided over several treatment sessions to avoid exposing healthy tissue to unnecessarily high single doses. However, for younger patients, the doses are typically lowered, resulting in more individual treatments and doctor visits, making the procedure very long and expensive. The side effects from this type of procedure include erythema and desquamation of the skin. The advantage of this type of therapy is that surgery can be avoided, allowing patients in poor health or with coagulation issues to use this treatment path. In addition, this type of therapy may be preferred in the case of large lesions, because surgery for these lesions can very complicated. The recurrence rates vary depending on the lesion, but a common figure is 15%.

Finally, there are a few chemical treatment methods that are being developed. Photodynamic therapy uses a photoreactive agent to destroy the cancerous cells (the agent turns oxygen into a reactive oxygen species, ROS). In this procedure, the agent is injected in the blood stream and accumulates in the cancerous cells. When these cells are exposed to light, the agent is activated and the ROS quickly reacts with surrounding organic compounds destroying the cells. Literature values for the recurrence rate vary depending on the skin cancer type with Bowen's disease showing less than 10% and SCC having over 60% recurrence rates. Topical chemotherapy is also used to treat pre-cancerous conditions and functions the same way as "classical" chemotherapy. However, unlike systemic chemotherapy, the cell killing drug stays confined to the surface of the lesion instead of spreading through the entire body. This limits the side effects encountered with full chemotherapy but also limits the use of the method since the treatment will not reach deeply into the skin. Topical chemotherapy achieves low recurrence rates that are comparable to radiotherapy (below 15%). Both of these methods cause skin irritation and sun sensitivity (especially photodynamic therapy) and side effects include erythema, itching, and pain at the source of treatment.

Radiation therapy (radiotherapy) is a medical treatment for cancer using ionizing radiation to destroy cancerous cells. Ionizing radiation is defined as radiation with sufficient energy to ionize atoms in the skin and organs it penetrates. There are two main forms of ionizing radiation: photons (X-rays, as discussed above, and γ-rays) and charged particles (β and α-particles mostly) with radically different behaviors. Photons are highly penetrating and are generally used as external treatment methods. However, photons deposit a dose all along their path damaging the cells in the process. Many current photon treatment methods involve the focusing of multiple beams on the tumor, which tends to decrease damage to cells outside the focal point.

Heavy charged particles, on the other hand (protons, α-particles, and charged nuclei), have an energy-dependent range and deposit their energy through collisions. These particles slow down as they traverse the medium and deposit a maximum dose near the end of their path at the so-called Bragg Peak. Since most of the dose is deposited at the Bragg peak, the surrounding tissue is less affected than in other therapies. The initial energy of the particle controls the depth at which the Bragg peak occurs, with higher energies corresponding to larger ranges. However, the facilities to produce these high energies are rare and very expensive to use.

β-particles are useful in treating superficial skin cancer lesions. A beta particle (beta ray or beta radiation) is a high-energy, high-speed electron (β−) or positron (β+) emitted by the radioactive decay of an atomic nucleus during the process of beta decay. β-particles have a high linear transfer and rapid fall off which means that they transfer energy quickly in the material (in this case, the skin) and their distribution stays similar to the geometry of the source. The advantages are twofold: the high linear transfer means that the particles do not penetrate very far into the tissue and that they generally do not affect tissue outside the region where they are generated. Since the particles do not penetrate deeply in the tissue, they don't interact with muscles and bones and they generally will be confined within the desired geometry—thus sparing the surrounding tissue. The main isotopes currently used in β-particle treatment are $^{177}$Lu, $^{90}$Y, and $^{131}$I.

There is a need for a skin cancer treatment that results in low recurrence rates, is less invasive, and more widely applicable than surgery, but limits damaging side effects, such as exposure of sensitive tissues. It is also desirable that the treatment does not require multiple visits, and is easily adaptable for treating lesions of varying size, shape, depth, and type.

The information included in this Background section of the specification, including any references cited herein and any description or discussion thereof, is included for technical reference purposes only and is not to be regarded subject matter by which the scope of the invention as defined in the claims is to be bound.

SUMMARY

The technology disclosed herein is related to a skin patch for treatment of various skin conditions in a subject, for example skin cancer. The skin patch includes a substrate, and a layer of an isotope deposited on the substrate. The isotope layer is substantially uniform and has a thickness that varies less than about 20%. The skin patch may further include an encapsulation layer, one or more additional isotope layers, a modulating layer, and/or a radioprotective layer.

In several embodiments, a method of manufacturing a skin patch for treating a skin condition in a patient is disclosed. The method includes preparing a substrate material; depositing at least one layer of an isotope on the substrate material to create an isotope film; adding an encapsulating material over the isotope layer to create an encapsulating layer; and irradiating the film with a neutron source to convert the isotope to a radioactive isotope.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments and implementations and illustrated in the accompanying drawings.

BRIEF DESCRIPTION OF THE DRAWINGS

FIG. 6 schematic views of sputtering guns at different angles. Panel a shows a gun at 0 degrees. Most of the sputtered atoms don't hit the sample and the center of the sample has very few atoms deposited onto it. Panel b shows a sputtering gun with a small gun angle (10 degrees). A bigger portion of the atoms hit the sample and the fluctuations in flux on the different sides of the sample even out through rotation of the sample. Panel c shows a sputtering gun with a moderate gun angle (17.5 degrees). The center has on average more atoms deposited onto it increasing the deposition rate relative to the sides of the sample.

FIG. 7 shows the variation of thickness over the range of the sample holder.

FIG. 8 Panel a shows thickness measurements (normalized by the mean thickness value on the plateau) along a silicon strip. The dashed lines indicate the region w where variation in thickness is less than 5%. The circled region shows the region in which the calibration data was taken. Panel b shows exemplary collected data from calibration runs. The slop of the line gives the calculated deposition rate of the sputtering system, 2.96±0.02 µm/h. The black dashed line gives the effective deposition rate on KAPTON®.

FIG. 9 shows a comparison of deposition rate on silicon from the rate on KAPTON.

FIG. 10A shows results from XRF measurements of an irradiated sample.

FIG. 10B shows results from XRF measurements of a sample that has not been irradiated.

FIG. 16 shows trace element data sorted by weighted production.

FIG. 26 shows a comparison between predictions and experimental results for each irradiation run.

FIG. 27A shows a sample centering device for the USGS detector.

FIG. 27B shows the USGS detector setup.

FIG. 28A shows a device used to position calibration sources.

FIG. 28B shows a device used to position calibration samples.

FIG. 31 shows the resulting efficiency calibration curve for the USGS detector of FIG. 27B.

FIG. 32 shows a comparison of calibration curves.

FIG. 33 shows a comparison between predictions and experimental results for additional irradiation runs with the USGS set up of FIG. 27B.

DETAILED DESCRIPTION

Figures 1, 2:
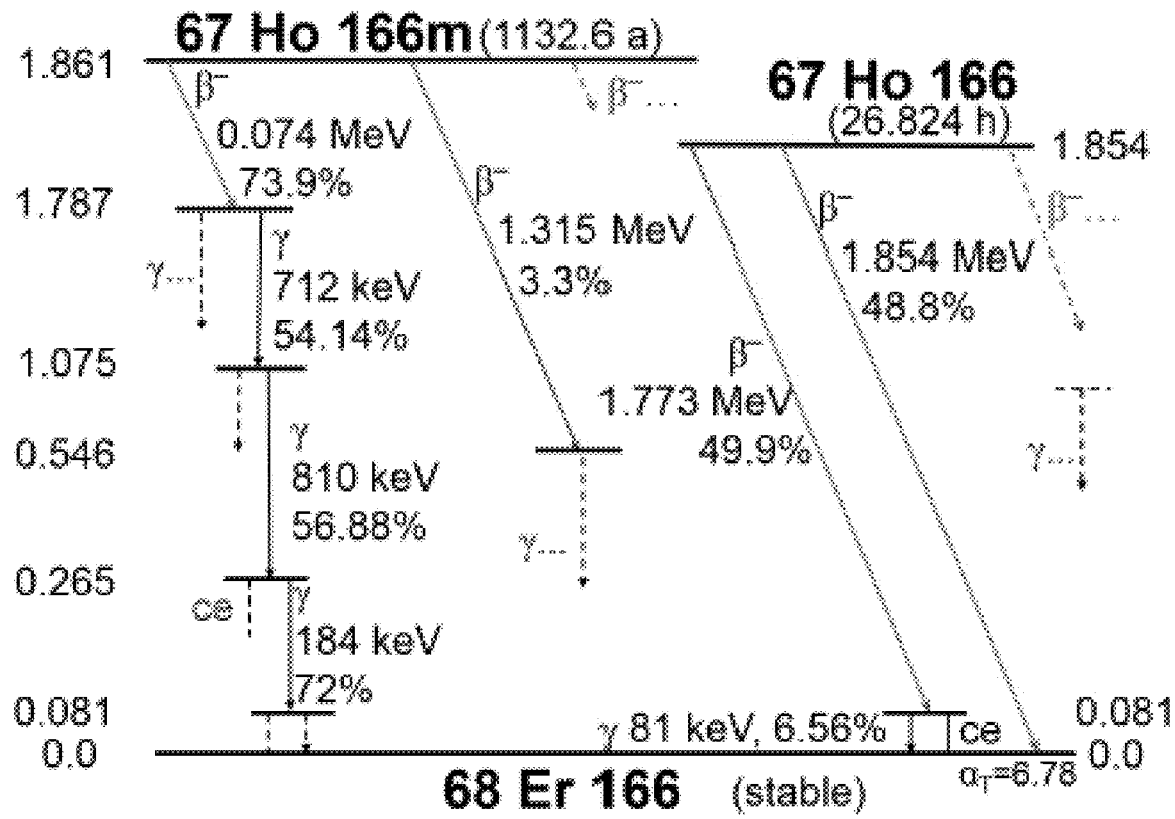
FIG. 1 shows the decay scheme for $^{166}$Ho to $^{166}$Er.
FIG. 2 shows various neutron capture cross sections for possible reactions of $^{165}$Ho.

This disclosure is related to a skin patch for treating skin cancer and a method of manufacturing such a skin patch to produce a skin patch of a reliable and reproducible thickness. The skin patch includes an element selected for its ability to be activated to an isotope having a short half-life, low toxicity, stable daughter isotopes, and availability. In one embodiment, the element may be phosphorus. In many embodiments, the skin patch may be made of an isotope in the lanthanide series (i.e. cerium, praseodymium, neodymium, promethium, samarium, europium, gadolinium, terbium, dysprosium, holmium, erbium, thulium, ytterbium, and lutetium). In many embodiments, the skin patch is made with stable naturally-occurring holmium-165. After activation by irradiation, some of the holmium-165 atoms become holmium-166 through neutron capture. In this example, holmium-166 is the radioactive isotope that is the active ingredient of the patch.

The skin patch of the present disclosure provides a type of radiotherapy where β-particles are used instead of γ-rays to provide a more contained radioactive dose. In this manner, the disclosed skin patch combines the advantages of radiotherapy (such as no need for surgery and application to wide variety of patients) with the benefits and precision of surgery. In some embodiments, the disclosed devices and methods may be useful in limiting damage from traditional radiotherapy and/or the need for recurrent treatments to arrive at the therapeutic dose (fractionation).

In several embodiments, the skin patch may consist of a thin film or foil of an element, such as a metal, deposited on a substrate, wherein the element is activated to create a radioactive isotope. In many embodiments, depositing of the isotope layer onto the substrate may be by various methods known to those of skill in the art, including, but not limited to, use of adhesive, sputtering, physical or chemical deposition, etc. The skin patch may be spatially uniform, having a thickness that varies less than about ±20%. The skin patch may provide a highly localized radiation dose to a diseased tissue while sparing neighboring healthy tissue. The skin patch may be shaped to match the contour of the lesion or tumor. In many embodiments, the skin patch consists of a layer of holmium-165 deposited on a substrate. In many embodiments, the substrate is inert and does not react with the deposited element or radioisotope. In some embodiments, the substrate is a polymer, such as a polyimide, and may be a sheet (i.e. a freestanding film), such as a polyimide film. In most embodiments, the polymer is rigid and generally resistant to degrading in high temperatures and radioactive environments. In some embodiments, the substrate is a strip or sheet, of, for example, KAPTON® available from Dupont. In some embodiments, the substrate may have an adhesive backing, for example the substrate may be a tape, for example KAPTON tape.

In many embodiments a method of manufacturing the skin patch results in a reliable, uniform, and safe skin patch that can be reproducibly manufactured. The method may include one or more of cleaning the substrate, depositing a metal target uniformly across the substrate, and encapsulating the metal target. The method then includes an irradiation or activation step, in which the metal atoms are irradiated, and become unstable radioactive atoms. In some embodiments, the method may include an activity measurement step allowing a medical provider to select and/or tune the skin patch's activity. In addition, knowing the patch's activity may allow the medical provider to adjust the patient's exposure times. For example, a patch with high activity may allow short exposure times, while a patch with low activity may require longer exposure times to provide equivalent doses.

Skin Patch for Treating Skin Conditions

The skin patch of the present disclosure may be a thin film or foil physically deposited onto a flexible substrate (e.g., a polymeric or plastic sheet). The thin film or foil may include an element having a radioactive isotope selected for its half-life, toxicity, stability of daughter isotope, and availability. For example, an isotope may be selected with a half-life that is long enough to allow production of the patch and then application of the patch in a given time span (e.g., long enough to allow for delivery of the active patch to regional and national facilities and for application to a patient) sufficient to allow treatment, but short enough to allow for safe disposal after the patch is used. A short half-life makes the production and application process somewhat time sensitive, whereas a long half-life may lead to complications when trying to dispose of the patch after it is used. In one example, the radioactive isotope selected is holmium-166 (produced from neutron activation of stable holmium-165); however, other isotopes, for example phosphorus, or those in the lanthanide series may also be used. In several embodiments, the skin patch comprises an isotope layer of $^{165}$Ho deposited on a KAPTON sheet.

The skin condition for treatment with the disclosed skin patches and methods may include non-cancerous, pre-cancerous, and cancerous lesions. In some embodiments, the lesion is a basal cell carcinoma or squamous cell carcinoma.

Isotope Layer

The isotope layer may be various elements capable of absorbing and releasing radiation. In some embodiments, the isotope layer may be comprised of one or more elements that may absorb a neutron particle to transition to a radioactive isotope. In most embodiments, the radioactive isotope emits a beta-particle during decay. In many embodiments, the isotope layer comprises one or more elements of the lanthanide series, for example, cerium, praseodymium, neodymium, promethium, samarium, europium, gadolinium, terbium, dysprosium, holmium, erbium, thulium, ytterbium, and lutetium. In many embodiments, the isotope layer comprises holmium.

Holmium-166 is nontoxic to humans, has a half-life on the order of one day (26.8 hours), decays to a stable daughter nucleus ($^{166}$Er) without emitting high energy γ rays, and the isotope needed to produce it ($^{165}$Ho) through neutron capture occurs naturally, minimizing costs associated with purification or enrichment processes. FIG. 1 shows the decay scheme for $^{166}$Ho to $^{166}$Er. The β-particles emitted through this decay have a maximum energy of 1.8 MeV, allowing the particles to penetrate deep enough (e.g., about 3-5 mm deep into skin tissue) to destroy cancer. The low energy γ-rays and X-rays (e.g., <100 keV) produced during the relaxation of $^{166}$Er to its ground state do not penetrate very far into the skin and do not contribute significantly to the deposited dose. While it is possible to produce an excited, metastable state of $^{166}$Ho$^m$ with a half-life of 1200 years, and this state produces high energy gamma rays when decaying, the cross-section for producing this state is small and creates little to no additional activity.

Furthermore, holmium-165 has a relatively high thermal neutron capture cross-section, making the activation process feasible within a reasonable time at a neutron reactor. In some embodiments, neutron capture may take 5 min to 5 hours, for example about 15 min to 3 hours, or about 30 minutes to one hour. In most cases, the time for the activation process may depend on the required activity of the patch, the activity of the reactor, and the position of the patch being activated. FIG. 2 shows the various neutron capture cross sections for possible reactions of $^{166}$Ho. The cross sections for reactions other than $^{165}$Ho to $^{166}$Ho$^9$ coupled with the relatively short activation times make the other reactions less significant in the activity and dose calculations.

Figure 3:
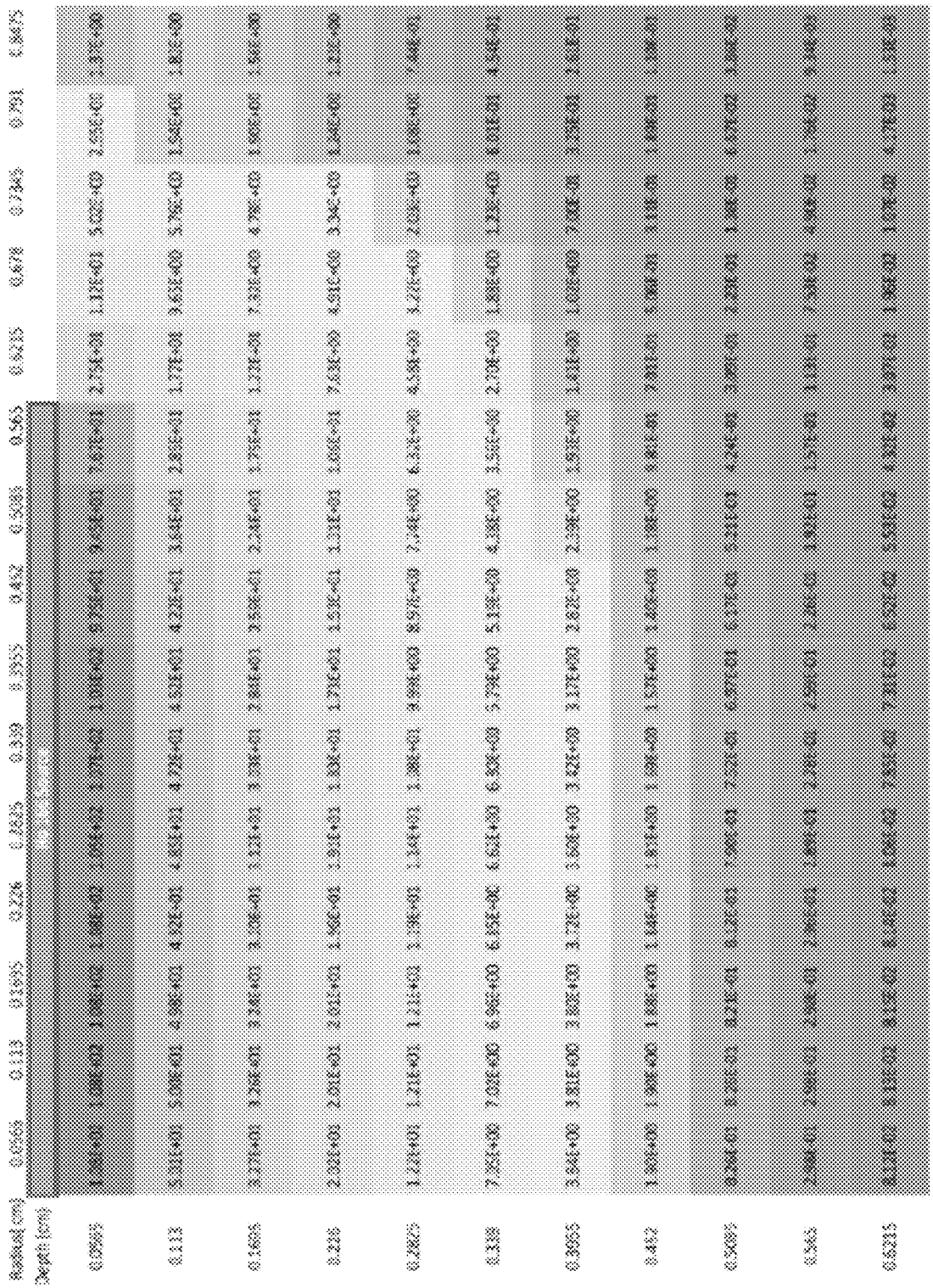
FIG. 3 shows a dose distribution profile for a $^{166}$Ho cylindrical source.

The following Equation 1 shows a rough approximation to calculate the dose deposited from β emissions in the skin:

$$D = \frac{E_{em}}{2M_{tissue}}$$

$$E_{em} = A \Delta t E_{decay}$$

$$M_{tissue} = \rho S d_{avg}$$

Where D is the deposited dose, $E_{em}$ is the total emitted energy from the β-particles, $M_{tissue}$ is the mass of skin the dose is deposited into, A is the activity of the patch, Δt is the duration of treatment, $E_{decay}$ is the average energy from a β-particle, ρ is the density of skin, S is the irradiated surface, and $d_{avg}$ is the average depth that the β-particles reach. The factor of 2 stems from the fact that the radiation is emitted isotropically and only half of it reaches the skin. For an example calculation, a density of skin equal to that of water (1 g/cm$^3$), a patch of 1 cm$^2$, an activity of 1 mCi, and a treatment time of 30 minutes are all assumed. The average energy of the β-particles from $^{166}$Ho can be calculated using the energy spectrum of the decay resulting in an average energy of 667 keV/decay. The same spectrum can be used to calculate the average penetration depth of the β particles, as shown in Equation 2 below:

$$d = aE\left(1 - \frac{c}{1+cE}\right)$$

Where a, b, and c are empirically fit parameters and E is the energy of the particle. Using a=0.55 keV$^{-1}$ mg/cm$^2$, b=0.9841, and c=0.003 keV$^{-1}$, the average penetration depth is calculated to be 4.2 mm. With all these parameters, the calculated deposited dose is ≈9 Gy (J/kg). This estimated dose shows that 1 mCi is a high enough activity to approach therapeutic dose levels, which may be between 10-75 Gy, and preferably between about 35-50 Gy. This is an order of magnitude calculation and specialized software like VARSKIN can be used to simulate the dose profile in the skin, especially to calculate the dose deposited from γ-rays. FIG. 3 shows the result from such a simulation.

The patch of the present disclosure has a thickness that is selected for a therapeutic dose of radioactivity from the radioactive isotope layer of the activated skin patch. For example, the patch may comprise a thin film of isotope layer wherein the thickness of the thin film or foil is selected based upon the amount of radioactivity to be delivered after activation and/or the duration of time between activation and use of the patch. In many embodiments the thin foil or film has a thickness between about 1 μm and about 250 μm, between about 10 μm and about 250 μm, between about 25 μm and about 125 μm, between about 0.1 μm and about 10 μm, between about 1 μm and about 3 μm, or between about 1 μm and about 5 μm. The thickness of the film or patch may be fairly uniform. Rolled holmium foils of various thicknesses are available from commercial vendors, for example Goodfellowusa.com. For example, there may be less than 1%, 2%, 3%, 4%, 5%, 6%, 7%, 8%, 9%, 10%, 11%, 12%, 13%, 14%, 15%, 16%, 17%, 18%, 19%, 20%, 21%, or 25% thickness variations over the area of the patch or isotope layer. In another example, there may be less than 5%, 10%, 15%, 20%, or 25% thickness variations over about 2.5 cm (1 inch) radius circle around the center of the patch.

The isotope layer may be deposited upon a substrate using various methods. In many embodiments, the isotope layer is deposited as a pre-formed foil or film layer. In other embodiments, the isotope layer may be chemically or physically deposited, or sputtered onto the substrate. In some embodiments, an adhesive layer may be between the isotope layer and the substrate layer. In some embodiments, the substrate layer may include one or two layers of an adhesive, for example the substrate may be self-adhesive, such as a tape.

The skin patch of the present disclosure has a geometry that follows that of the malignancy. For example, the skin patch may be shaped to match the contour of the lesion or tumor. The skin patch may be cut to the desired shape after it is produced or a mold or shadow mask may be used to shape the skin patch as a stable isotope is deposited on a substrate to form the skin patch.

The skin patch may be comprised of one or more layers of an isotope. In some embodiments, the isotope layer may comprise sub-layers of different thickness and/or different elements. For example, where more radiation is to be administered to a portion of a patient's lesion, the patch may have multiple layers of an isotope foil or film, while in other areas, where less radiation is to be administered, the patch may, in some embodiments, have fewer layers. In some embodiments, masks or molds may be used during deposition of the isotope so that areas of the patch may have two or more layers of the isotope. In these embodiments, the activity of the activated patch may be greater in an area having multiple layers of the isotope. In various embodiments, the layers may be of the same or similar thicknesses, while in other embodiments the layers may have differing thicknesses. In most cases, each layer may have a substantially uniform thickness that varies less than about 5%, 10%, 15%, 20%, or 25%. In some embodiments the second layer deposited may have an area that is greater than the area of the first layer, while in other embodiments, the area of the second layer is less than the area of the first layer.

The skin patch may be neutron activated through an (n,γ) reaction. The patch may be activated by a reactor that is capable of activating enough isotope to become a radioactive isotope that can achieve therapeutic activity ranges. For example, a therapeutic dose may be around 35 to 50 Gy. For example, the 1 MW TRIGA reactor at the Federal Center in Lakewood, CO can achieve this result. Assuming a 30-minute application on a patient, the typical activity of the patch should be around 2 mCi for a 1 cm$^2$ patch to achieve therapeutic dosage levels. Irradiation time at the reactor may vary given neutron fluence at the irradiation position and the amount of $^{165}$Ho deposited on the patch.

The patch may be applied to a patient by a medical practitioner. The patch may include a handle to protect the practitioner from unnecessary radiation exposure during application of the patch to the patient and to help guide the application of the patch on the patient. The handle may be made of a material that absorbs radiation and helps to reduce the amount of exposure for the medical practitioner. The handle may be made of a thick material. In one embodiment, the handle is made of aluminum. The handle may be detachable. For example, once the patch is applied to the patient, the handle may be removed and discarded or reused with another patch.

Method of Manufacturing the Radioactive Isotope Skin Patch

A method of manufacturing a skin patch is disclosed. In many embodiments, the skin patch may be constructed of at least one layer of an isotope having a thickness that is spatially uniform, reliable, and reproducible. Spatial uniformity of the layer may help to provide a uniform dose of radioactivity from the skin patch after the patch is activated. In some embodiments, as discussed above, the skin patch may be manufactured with areas of greater of lesser thickness. In this manner, the patch may generate a more uniform radiation profile where the target lesion is uniform, and a variable radiation profile where the target lesion is variable. This ability to tailor the activity of the skin patch has significant advantages over existing techniques, for example those that use solution processing that creates irregular and uncontrolled dosages across the lesion.

The thickness of the isotope deposited on the substrate is selectable, depending upon the amount of radiation to be administered, the time between activation of the patch and application to the patient. In many embodiments, the thickness of the isotope layer in the skin patch may be between about 0.7 microns (μm) and about 250 μm, about 0.7 μm and about 3.5 μm, about 10 μm and about 250 μm, and about 25 μm and about 125 μm. For example, the thickness of one isotope layer may be 1-3 μm. In some embodiments, the skin patch may comprise 1 or more layers of deposited isotope, such as more than 1, 2, 3, 4, 5, 6, 7, 8, 9, and 10 layers, and less than about 15, 10, 9. 8, 7, 6, 5, 4, 3, or 2 layers. In some embodiments, the layers may have the same or differing shapes, and/or may be comprised of the same or different isotopes.

The disclosed method of manufacturing a skin patch may prevent or reduce cracking or flaking of the deposited isotope layer. In some embodiments, the isotope layer is derived from a rolled film or foil, cut to size, and deposited onto the substrate layer. In many embodiments, flaking is minimized to reduce the risk of radioactive isotope separating from the skin patch, resulting in unwanted contamination. In several embodiments, the selection of the metal target material, and the cleaning of the substrate material can aid in producing a skin patch with a desired thickness and prevent the skin patch from flaking. In several embodiments, metal (e.g. pure holmium metal), rather than a metal oxide (e.g. holmium oxide or $Ho_2O_3$), may be used as the target material. A metal, non-oxide, target may allow for higher deposition rates than a metal oxide target.

The disclosed method may include a deposition process and an activation process and one or more of a cleaning process, a sizing process, a stress test, and an encapsulation process. In some embodiments, the substrate is first cleaned before the isotope is deposited on the substrate. Cleaning may help to reduce or prevent flaking or separation of the isotope layer during or after the deposition process. In many embodiments, dust and other impurities or contaminants on the substrate surface may prevent or reduce adhesion between the substrate and the stable isotope. Dust or other contaminants may be removed from the surface of the substrate by cleaning. As one example, the substrate may be cleaned with a solvent, and then dried with compressed air. In some embodiments, the solvent is a cleaning solvent and the air is nitrogen or another inert gas that helps to remove or evaporate the residual solvent from the substrate. In some embodiments, the solvent may be acetone and/or isopropanol, and the gas may be compressed nitrogen. Where a second substrate material is placed near the skin patch substrate material to help in determining the thickness of the deposited layer, the second substrate material (e.g. silicon) may be cleaned in the same or a similar way.

The disclosed substrate is selected based on one or more characteristics of temperature resistance, solvent resistance, radiation resistance, charge, rigidity, flexibility, formability, etc. In most embodiments, the substrate is manufactured from a material that is resistant to one or more solvents used to clean the substrate. In several embodiments, the substrate is a flexible solid polymer, plastic, or foil. In several embodiments, the substrate is a polyimide substrate. In many embodiments, KAPTON may be used as the substrate.

Once the substrate is cleaned, the stable isotope may be deposited on the substrate by various means. For example, sputtering, thermal evaporation, or chemical vapor deposition may be used to deposit the isotope onto a plastic sheet.

As one example, thermal evaporation may be used to deposit the isotope on the substrate. In thermal evaporation, the substrate (e.g. a KAPTON® sheet) and the desired stable isotope material are loaded into a vacuum chamber. The isotope material is placed in a crucible or a "boat" and heated in a controlled manner until the isotope material begins to sublime or evaporate. The isotope material impacts the substrate sheet, depositing a layer of the isotope material on the substrate sheet. In many embodiments, thermal evaporation may result in a very uniform layer of deposited isotope material, for example less than about 10%, 5%, or 2% variation in thickness of the deposited layer. As another example, electron beam-evaporation may be used to manufacture the disclosed skin patches. In this technique, the isotope material is placed into a crucible and heated by directing a beam of electrons at the surface of the isotope material. In some embodiments, electron beam evaporation may reduce the need to heat the entire volume of isotope material, limiting heating to the surface of the isotope material. In many embodiments, electron beam evaporation may result in the same or similar evaporation rate, and allow, for example, the evaporation and deposition of materials that would normally react with the material of the crucible at high temperatures.

Sputtering may also be used to deposit the isotope material onto the substrate. Sputtering uses a gas to knock off atoms from the target material onto a substrate. In some embodiments, the substrate may be rotated to enhance the uniformity of the deposited layer. Argon gas is usually used for sputtering, as it is inert and relatively heavy, which makes sputtering of heavy elements easier and more effective. As one example, DC (direct current) sputtering may be used. In one embodiment, stable holmium-165 may be deposited on a KAPTON sheet using DC sputtering. In some examples, $^{165}$Ho is deposited on the substrate with a thickness of about 2 µm. In other embodiments, the thickness of the $^{165}$Ho layer may be less than or greater than 2 µm. In one embodiment, the system is a DC sputtering system, for example a system manufactured by AJA International Inc.

Argon gas may be used to sputter holmium metal on a substrate. In these embodiments, argon ions may be accelerated on Holmium metal, such that knocked-off Ho atoms are ejected toward the KAPTON substrate. A large voltage difference is applied between the target and the sample that accelerates stray electrons. In many embodiments, sputtering may result in high source utilization.

In some cases, such as where the substrate targets are insulators, RF (radio frequency) sputtering may be used. In this technique, the electrical potential of the current in the vacuum environment is alternated at radio frequencies to avoid a charge building up on certain types of sputtering target materials, which over time can result in arcing. In this technique, AC voltage helps to avoid charge buildup on the target. If these electrons collide with argon atoms, they can ionize them and release additional electrons creating a cascade. This cascade forms an argon plasma that accelerates towards the target. Argon ions can knock atoms off the surface of the target through elastic collisions. The sputtered atoms are ejected towards the sample and are not deflected by the electric field as they stay neutral during the collision process. Equation 3 below shows that maximum energy transfer is achieved when the masses of the ion and sputtered atom are equal:

$$E_{atom} \propto \frac{4m_1 m_2}{(m_1 + m_2)^2}$$

Depending on the atomic mass of the target, different sputtering gases may be used to maximize the deposition rate. However there are other considerations, such as cost, which can heavily influence the choice of sputtering gas. In some embodiments, the sputtering gas may be selected from argon, xenon, neon, etc.

Figure 4:
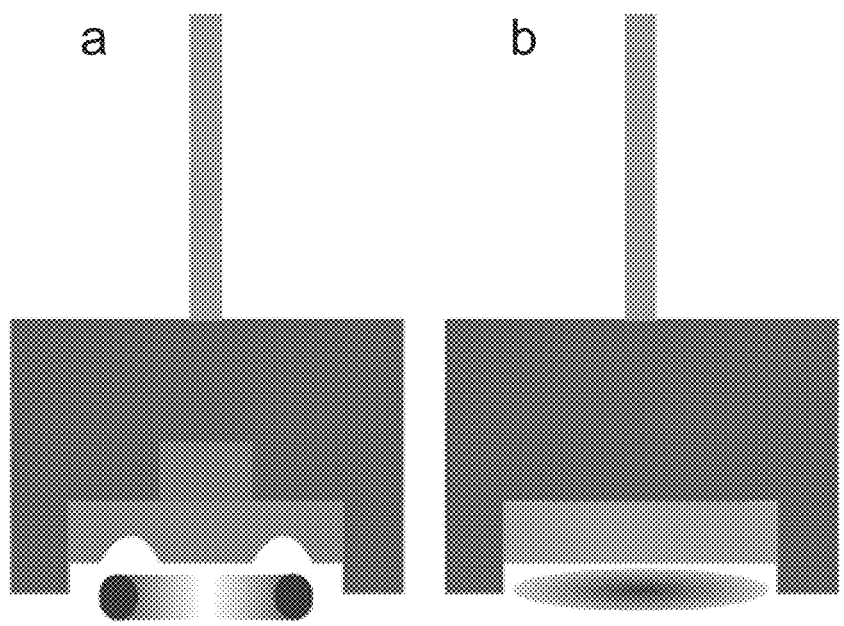
FIG. 4 Panel a shows a schematic representation of a magnetron sputtering section. The plasma (purple) is confined by a magnet (orange) and creates a typical "race-track" erosion profile on the target (gray). Panel b shows a schematic representation of a "standard" sputtering system. The plasma is not as confined as in the previous case and wears the target down more uniformly with the fastest wear occurring at the center.

Another sputtering system that may be used with the present method is magnetron sputtering, where a large magnet is used to confine the plasma to a circular region on the surface of the target, increasing the number of collisions with the target and therefore the sputtering rate. FIGS. 4A-4B show a schematic representation of a sputtering system with and without a confining magnet. FIG. 4A shows a schematic magnetron sputtering section in which the plasma is confined by a magnet and creates a typical "race-track" erosion profile on the target. FIG. 4B shows a schematic section of a "standard" sputtering system. The plasma is not as confined as in FIG. 4A and wears the target down more uniformly with the fastest wear occurring at the center. Sputtering systems usually operate at higher pressures than other deposition methods as they rely on a cascading effect to generate the plasma. However, if the pressure is too high, the electrons collide with neutral atoms before having enough energy to ionize them.

Figure 5:
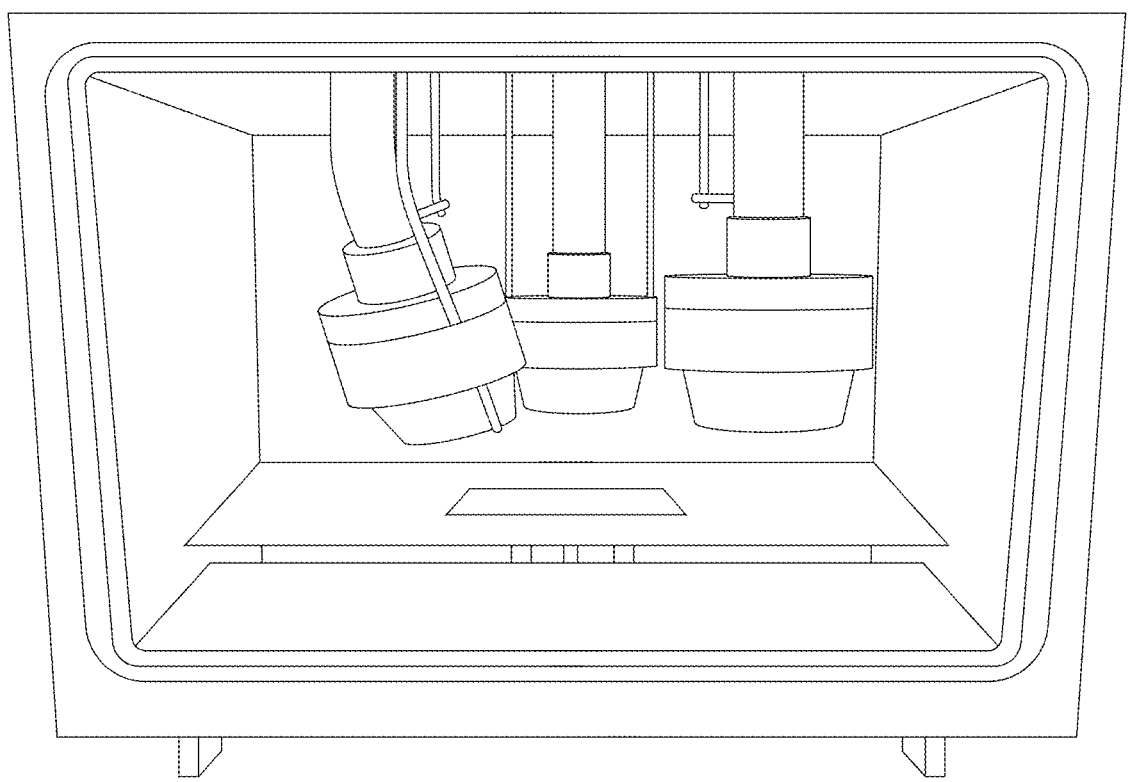
FIG. 5 is a picture diagram of the inside of a DC magnetron sputtering system.

In one embodiment, the disclosed method may use a DC magnetron sputterer, since holmium is conductive. FIG. 5 is a picture diagram of the inside of such a system. As shown in FIG. 5, the system may have more than one sputtering "gun". In some embodiments, the system may include three sputtering guns, which may allow loading of three different targets. One or all of the guns may be used to deposit a target on a substrate. In some cases, straight-on evaporation may yield low uniform deposition. In some embodiments, rotation of the substrate and/or angling of the substrate relative to the target may improve the uniformity of the deposited layer.

The substrate may be fastened to the sample holder using a variety of devices and techniques, including spring plates, clips, clamps, adhesives, etc. A second substrate material, for example silicon, may also be fastened to the sample holder. The second substrate material may be useful in estimating the deposited thickness of the stable isotope material onto the first substrate, especially where it is problematic or difficult to estimate the thickness of the deposited isotope layer on the first substrate. In most embodiments, the substrate may be centered on the sample holder to remove spatial variations of the deposition rate and nonlinear effects in deposition rate. Centering the sample may also create a large region of uniform deposition. With no nonlinear effects in the deposition rate, predicting the thickness of the patch sample may be easier, and may help to create a more reliable patch.

A profilometer may be used to measure thickness variations both in time and position of the target on the substrate. The profilometer may include a stylus that may be dragged over the substrate to measure the thickness of a deposited material at an edge. Use of a profilometer may provide more accurate results where the surface is hard and/or flat. In these embodiments, a second substrate material, for example silicon, may be positioned on or near the first substrate material to aid in measuring the thickness of the deposited layer on the first substrate. For example, in some embodiments, KAPTON may lack a hard and/or flat surface, making accurate measurement of the deposited isotope layer difficult. However, in many embodiments, adhesive KAPTON tape may be used to create a sharp edge of deposited materials. To test deposition uniformity, material may be deposited on a strip of silicon spanning the entire width of the sample holder.

The mass of isotope material deposited on the substrate may be measured. In some embodiments, x-ray fluorescence may be used to measure the uniformity of a deposited isotope layer. In some cases, x-ray fluorescence may also be useful in providing the thickness, especially where the x-ray fluorescence device is well calibrated.

Varying the sputtering gun angle and position on the substrate holder may change the thickness of the isotope layer deposited on the substrate. FIGS. 6A-6C show a schematic view for the different gun angles and their potential effects on thickness. The sputtering guns each have a plasma, a target, and a magnet concentrating the plasma. The target may be lodged below the face of the gun creating a shadowing effect at low angles, this may, in some cases, reduce the deposition rate. FIG. 6A shows the gun at a zero degree angle. In this case, most of the sputtered atoms do not hit the sample or substrate and the center of the sample has very few atoms deposited onto it. FIG. 6B shows the gun at a small angle (for example, at 10 degrees). A bigger portion of the atoms hit the sample than in FIG. 6A and the fluctuations in flux on the different sides of the sample may even out when the sample, and substrate, are rotated. FIG. 6C shows the gun at a moderate angle (for example, at 17.5 degrees). In this embodiment, the center of the substrate sample may have more atoms deposited (and at a higher rate) relative to the sides of the substrate sample. FIG. 7 shows the variation of thickness over the range of the sample holder.

Deposition rates and thickness uniformity may be controlled in various ways. There are two main effects to take into account: first, the chosen gun angle affects the uniformity of the deposition with smaller angles relative to the vertical depositing more uniform films; second, higher angles relative to the normal achieve higher deposition rates in the middle of the sample holder. This can be deduced from FIGS. 6A-6C since small angles prevent a large portion of the sputtered atoms from reaching the sample. In one embodiment, a 10 mm gun setting (corresponding to a 17.5 degree tilt) may be selected, which may maximize the deposition rate and produce a region around the center where thickness is fairly uniform (less than 5% variation, as shown at FIG. 8A). For example, FIG. 8A shows thickness measurements (normalized by the mean thickness value on the plateau) along the length of a silicon strip. The dashed lines indicate the region where the variation in thickness is less than 5%. The circled region shows the region in which the calibration data was taken.

The deposition rate may be calculated and the extent to which this rate is linear as a function of time may be determined. To determine the deposition rate, data may be collected at varying time intervals. For example, data may be collected at 10, 20, 30, 45, and 60 minutes sputtering time and then fit to a line. The slope of the line is the calculated deposition rate. FIG. 8B shows an exemplary resulting calibration curve with a linear behavior visible from the fit. In this case, the deposition rate is 2.96±0.02 μm/h (at 100 W, 17.5 degree gun tilt, 10 mTorr argon pressure), which is high enough to produce samples of appropriate thickness in an hour. The deposition process may take about 30 minutes to an hour. The black dashed line gives the effective deposition rate on KAPTON.

In some cases, measuring the thickness of holmium deposited on silicon may accurately predict deposition on KAPTON. For example, FIG. 9 shows the deposition rate on silicon may be different from the rate on KAPTON. This table shows the mass expected to deposit on KAPTON using the thickness measured on the silicon as well as the actual mass that was deposited on KAPTON.

Applicants have discovered that differences in deposition thickness may be due to a charging effect on the KAPTON sheet surrounding the sample. Without wishing to be limited by theory, such charging effect may result in deflecting some of the incoming holmium atoms from the substrate, thus decreasing the deposition rate.

Figure 11:
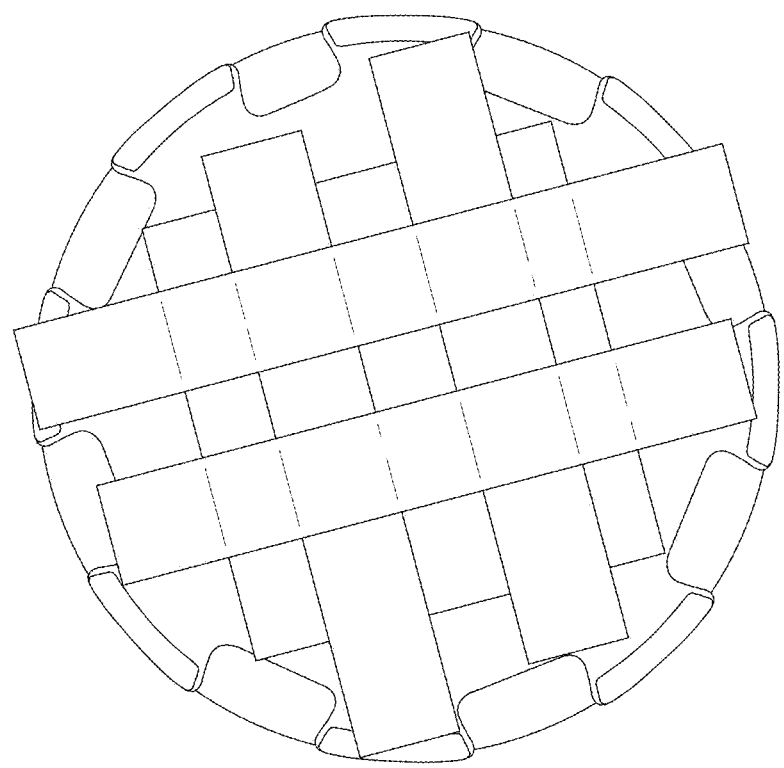
FIG. 11 shows a comparison between deposition on KAPTON and silicon substrate.

To characterize the holmium surface on KAPTON, specifically the uniformity of the surface, X-ray fluorescence (XRF) may be used. FIGS. 10A-10B show exemplary results from XRF measurements. These studies identify a relative uniformity, and a constant gradient from one edge to the other of the patch (e.g., a gradient across the sample from front to back). This gradient may be the result of yet another charging effect. For example, different charged areas may form on the KAPTON mask. As shown in FIGS. 10A-10B, the thickness variation is less than 10% from one edge of the sample to another, for example less than about 10%, 9%, 8%, 7%, 6%, 5%, 4%, 3%, 2%, or 1%. In FIG. 10B, there is a scratch on the surface of the sample that is visible where the surface dips down drastically. FIG. 11 shows a taping scheme used on the KAPTON. In this example, the left substrate is KAPTON, while the right substrate is silicon. As shown, the KAPTON has little to no deposition, while the silicon has deposition but the metal is discolored through oxidation. Because a mask may consist of several different strips of tape on top of each other, it is possible that different charged areas may form on the mask modulating the deposition onto the KAPTON. Specifically, in this example, the center piece of tape between the two samples could charge up and deflect more atoms from the center, decreasing the thickness along it and creating a gradient between the "center" edge and the outside edge of the sample.

Sizing the Skin Patch

The sizing process shapes and sizes the skin patch of the present disclosure to a shape and size that matches the shape and size of the lesion. By shaping the mask to the tumor, damage to nearby healthy skin and tissue is reduced. The sizing process may occur prior to the cleaning process, after cleaning, during the deposition process, or after the deposition process. For example, the substrate may be shaped prior to cleaning, such that the isotope of interest deposits on a pre-shaped substrate to form a patch that is shaped similarly to the pre-shaped substrate. As another example, the patch may be shaped using a mold during the deposition process. For example, a mold in the shape of the lesion may be placed on the substrate, and the metal target may be directed to inside the mold, depositing on the substrate within the mold and forming a patch of the desired shape. As an additional example, the patch may be shaped during the sputtering process by using a shadow mask or post deposition etching. In some embodiments a mask may be used that is shaped to match the shape of diseased tissue to be treated. As yet another example, the patch may be cut to the desired size and shape after the deposition process.

Skin Patches with Controlled Thickness

Skin lesions, for example skin cancer, may be non-uniform in shape and depth. For example, cancer cell growth may vary resulting in greater density and/or depth of cancer cells in some areas of the lesion. In some embodiments, the skin patch may be modified to conform to a non-uniform lesion, while minimizing damage to healthy tissue. For example, the radiation pattern and or density of the skin patch may be tuned. In most embodiments, tuning the disclosed skin patches may be achieved by performing one or more of various modifications to production of the skin patch.

The radiation dose from the skin patch delivered to skin may be tailored in various ways. In one embodiment, the radiation delivered at one area of the lesion may be altered by modifying the thickness of the isotope deposited on the substrate at that area. As described above, where a greater amount of radioactivity is desired at a given area, that area may receive additional deposition of the isotope. This may be achieved by depositing two or more layers in the area, resulting in the build-up of greater isotope thickness. After activation, for example by neutron capture, the area having greater thickness will have a greater radioactivity than areas with less thickness. In other embodiments, a thicker layer of deposited isotope at a given area could be reduced prior to activation. In these embodiments, a layer of deposited isotope could be subjected to wet-chemical or dry-plasma etching to remove a portion or all of the deposited isotope. For example, a thick layer to be activated later could be deposited and part of the film removed using an etch process.

Skin Patches with Tunable Dosing

The radiation dose pattern of a skin patch may be modified by adding one or more layers of an absorbing or modulating material over the deposited isotope layer and/or encapsulation layer. In these embodiments, the skin patch may possess a uniform layer of deposited isotope material, and the absorbing/modulating/modulation layer could be positioned over areas where less radioactivity is desired. For example, a thin layer of modulating material would be placed on the skin patch, or positioned between the patient and the skin patch to moderate the dose. In these embodiments, the modulating layer material would help to absorb all or a portion of the radiation, thereby reducing the energy of the radiation reaching the patient. This modulating material could cover the entire patch to moderate the dose over the entire area, or it could cover a part of the area of the skin patch to help in creating a pattern of radioactivity that is tailored for the depth and/or density of the target cells in the lesion. The disclosed modified skin patches may deposit the highest energy and dose to the deepest, densest, and/or most diseased areas of the lesion, while limiting the deposited dose at areas with less extensive disease penetration.

Moderating and/or radiation-dose shaping may be achieved by modifying the thickness of the deposited thin film or foil isotope layer(s), adding a modulating material to the skin patch, and/or by positioning a modulating or radioprotective material between the skin patch and the lesion. In some embodiments the modulating material is applied to the patch, either inside or outside of the encapsulation material. In some embodiments, the modulating material may also be an encapsulation material, and the patch may comprise a combined modulation/encapsulation layer. In some embodiments, the modulating material may be applied to the patient's skin before the patch is applied.

The modulating layer material may be various materials. In some embodiments, the modulating material may be a thin film of a metal, for example aluminum, a hydrocarbon based polymeric material, or a silicone polymer based material. In some embodiments, the modulating material may block all or some of the radioactivity from the skin patch. In some embodiments, fabricating the modulating material from aluminum may provide for very thin layers, while other materials, such as polymeric materials, may allow for ease of shaping and conforming them to the contours of the lesion. In many embodiments, silicon-based polymers may provide a larger mass of silicon and oxygen relative to hydrocarbons, which may allow for a higher amount of energy to be absorbed in a given thickness of modulating material. In most embodiments, the use of silicone-based modulating layers may provide for a softer and more comfortable skin patch that may conform to the contours of the surface of the lesion.

Modulating layer material may be positioned around the lesion to protect unaffected tissue from exposure to radiation. In these embodiments, a modulating layer may be positioned around the diseased area to aid in absorbing and/or blocking radiation from the skin patch. The use of protective masks may prevent healthy tissue from receiving an excessive dose of radiation and may also help to reduce the required accuracy of the medical practitioner in placing the patch at the lesion.

Stress Testing the Skin Patch

The resilience of the deposited film to stresses may be tested. Such a stress test may simulate application of the patch to an area of the body with high curvature. For example, the resilience may be tested by bending and rolling the film. A scanning electron microscope may be used to check the film surface for cracks and flaking of the isotope, for example, of holmium.

Encapsulation Layer

An encapsulation layer may be deposited over the isotope layer(s) to aid in minimizing or preventing flaking of the deposited layer. In some embodiments, flaking may occur after deposition of the isotype layer, removal of the patch from the sample holder, shaping of the skin patch, shipping, activation, and/or during application of the skin patch to the lesion. An encapsulation layer may aid in reducing or preventing release of radioactive material, and contamination of the patient's skin or the skin of the medical practitioner.

The encapsulation layer may be made of various materials. In some embodiments, the encapsulation layer is made of a polymer. In some embodiments, the encapsulation layer may be a thin layer of substrate material. In most embodiments, the encapsulation layer may absorb little or no radioactivity during activation or radioactivity from the skin patch after activation. For example, the skin patch may be encapsulated with an adhesive layer of the substrate, such as a tape, for example KAPTON tape. In many embodiments, the encapsulation layer may prevent the isotope, for example holmium, from flaking before or after activation. As another example, the encapsulation layer may also be vapor deposited on the isotope layer. In some embodiments, the encapsulation may be a plastic, for example p-xylylene, such as poly(p-xylylene) or variant thereof. In some embodiments, the plastic derived from [2.2]paracyclophane that is converted to p-xylylene and deposited on the deposited isotope layer. In some embodiments, the plastic is derived from PARYLENE, PARYLENE C, PARYLENE N, PARYLENE D, PARYLENE HT, and/or PARYLENE. The encapsulation layer may also be applied with a thermal laminator into a pouch. In many embodiments, the encapsulation layer may act as a secondary containment, and not a primary containment. Existing techniques may include a primary containment, for example bandage, which shed particles that must be encapsulated. In this manner, the fabrication method of the present disclosure may eliminate particulates.

Radioprotective Layer

A radioprotective layer may be positioned between the isotope layer and the patient's skin to protect the patient's skin that is not to be treated from exposure. In some embodiments, the radioprotective layer may allow a practitioner to use a patch having an area that is greater than the area of the patient's skin to be treated. In some embodiments, the disclosed patch may comprise a modulating layer and a radioprotective layer, while other embodiments may comprise a modulating layer or a radioprotective layer. In some embodiments the modulating layer may be a radioprotective layer or the radioprotective layer may be a modulating layer. The radioprotective layer may be manufactured of a material that absorbs most or all of the radiation from the activated patch, but is able to be shaped by the practitioner to conform to the shape and size of the lesion or skin to be treated. For example, the radioprotective layer may be made of a similar or the same material as the modulating layer. For example, the radioprotective material may be a thin film of a metal, for example aluminum, a hydrocarbon based polymeric material, or a silicone polymer based material. In some embodiments, fabricating the radioprotective material from aluminum may provide for very thin layers, while other materials, such as polymeric materials, may allow for ease of shaping, flexibility, and/or the ability to conform the patch to the contours of the skin and/or lesion. In many embodiments, silicon-based polymers may provide a larger mass of silicon and oxygen relative to hydrocarbons, which may allow for a higher amount of energy to be absorbed in a given thickness of radioprotective material. In most embodiments, the use of silicone-based radioprotective layers may provide for a softer and more comfortable skin patch that may conform to the contours of the surface of the lesion. In several embodiments, the radioprotective layer is thicker than the modulating layer described above.

The radioprotective layer material may be positioned around the lesion to protect unaffected tissue from exposure to radiation. In these embodiments, a radioprotective layer may be sized and shaped to reflect the outline of the skin to be treated, and the radioprotective layer may be positioned around the diseased area to aid in absorbing and/or blocking radiation from the skin patch. Use of the radioprotective layer may prevent healthy tissue from receiving an excessive dose of radiation and may also help to reduce the required accuracy of the medical practitioner in placing the patch at the lesion.

Predicting Skin Patch Activity

In some embodiments, it may be useful to accurately predict the dose of radioactive material that will be delivered to a patient, as a larger dose can cause harmful side effects, and smaller doses may have limited effectiveness. Both predictions of the activity of a given patch and actual measurements of the activity of that patch can be used to determine proper exposure times. As one example, the activity of a produced skin patch may be predicted by weighing the sample. To measure the activity of the produced skin patch, the skin patch can be activated using a reactor that is capable of activating enough of the radioactive isotope to achieve therapeutic activity ranges. The detectors used to measure the activity of the patches may first be calibrated. For calibration, a substrate is used that may be any material or composition that has a smoothness and hardness that is ideal for profilometry. For example, silicon may be used as a substrate for calibration. The actual measurements take into account possible impurities of the patch. Deviations in the actual measurements from the predicted activity can be adjusted, for example by changing exposure times. In some embodiments, if a sample is produced with a higher activity than expected, the exposure time can be reduced to adjust the dose accordingly. A target exposure time is about 30 to 60 minutes to deliver a therapeutic dose. These measurements can also be used to verify whether there are any large amounts of secondary radiation which could significantly increase the deposited dose to the patient. In this manner, using radiation measurement techniques, the dose deliverable to a patient may be determined with precision.

Specific Embodiments

Figure 34:
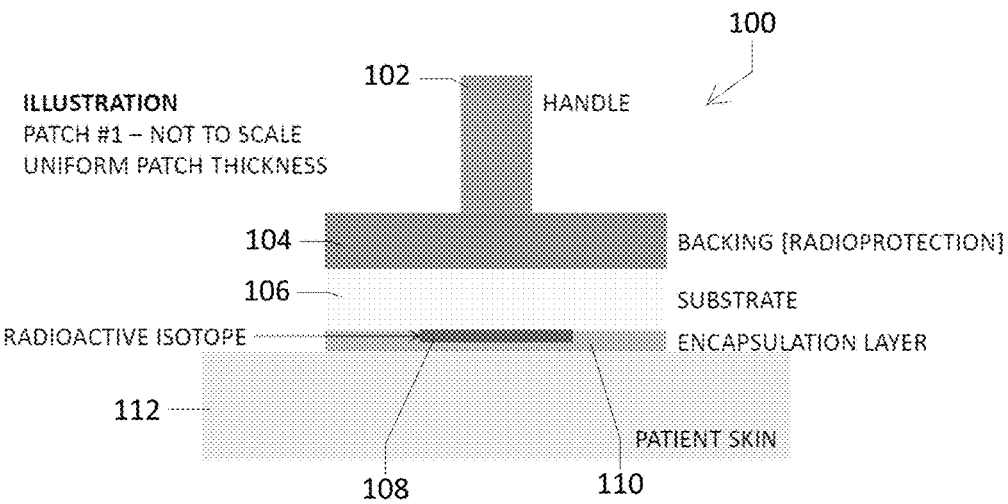
FIG. 34 is a schematic illustration of one embodiment of the disclosed patch positioned against a patient's skin.

Several embodiments of the proposed patch are depicted in FIGS. 34-38. FIG. 34, for example, depicts one embodiment of the disclosed skin patch having an isotope layer of uniform thickness, wherein the patch has been activated to transition the isotope layer to a radioactive isotope layer. In this embodiment, the disclosed patch 100 comprises a handle 102, backing layer 104, substrate layer 106, isotope layer 108 (here activated), and encapsulation layer 110. The skin patch 100 is shown applied to a patient's skin 112. The handle 102 may be any shape that provides sufficient material and/or area for gripping, e.g., an ergonomic shape. In the depicted embodiment, the handle 102 has a rectangular or rod-like shape. As shown, the handle 102 is coupled to and extends from the backing layer 104. For example, the handle 102 may be coupled to the backing layer 104 by an adhesive, welding, or the like. The handle 102 may allow a medical practitioner to apply and remove the skin patch 100 without contacting the layers of the patch, for example the backing layer 104. As shown, the backing layer 104 extends across the entire upper surface of the patch 100; however, it is contemplated that the backing layer 104 may extend across a portion of the upper surface of the patch and/or may be formed by more than one layer. The thickness of the backing layer 104 may be selected to prevent radiation from passing through the upper surface of the backing layer, for example, exposing a medical practitioner and/or the patient to radiation from the isotope layer 108.

The backing layer 104 may be coupled to the substrate layer 106, for example by an adhesive, cohesive properties, welding, or the like. As shown in FIG. 34, the substrate layer 106 extends across the entire width of the patch 100. The substrate layer 106 may be a strip or sheet of material. In some embodiments, the substrate may have an adhesive backing, for example the substrate may be a tape to aid in adhering to the backing layer and/or the isotope layer. In the depicted embodiment, the substrate layer 106 is thicker than the backing layer 104; however, the substrate layer 106 may have the same or smaller thickness than the backing layer 104.

The isotope layer 108 may be deposited on, adhered to, coupled to, and/or formed on the substrate layer 106. As shown in FIG. 34, the isotope layer 108 is deposited on a lower surface of the substrate layer 106 (e.g., closer to the patient's skin 112 than the substrate layer 106). For example, the isotope layer 108 may be deposited on and/or coupled to the substrate layer 106 by an adhesive, e.g., an adhesive surface of the substrate layer 106 and/or a separate adhesive layer. In the depicted embodiment, the isotope layer 108 is centrally located on the substrate layer 106; however, it is contemplated that the isotope layer 108 may be positioned off-center. In the depicted embodiment, the isotope layer 108 has a uniform thickness. As shown, the isotope layer 108 is encapsulated or surrounded by the encapsulation layer 110 below and the substrate layer 106 above. The encapsulation layer 110 may be coupled to the substrate layer 106. For example, as shown, the encapsulation layer 110 couples to portions of the surface of the substrate layer 106 beyond the edges of the isotope layer 108. In this manner, the encapsulation layer 110 and isotope layer 108 together extend across the entire lower surface of the substrate layer 106. As shown, the encapsulation layer 110 is thinner than the backing layer 104 and substrate layer 106; however, it is contemplated that all three layers may be the same thickness, similar thicknesses, or different thicknesses. In some embodiments, the encapsulation layer 110 may be the same thickness as one of the other two layers. The encapsulation layer 110 may have a thickness selected to allow sufficient radiation (e.g., sufficient to effectively treat the skin condition) to pass from the isotope layer 108 to one or more cells of the patient's skin 112. In some embodiments, the encapsulation layer 110 may be coupled to the patient's skin 112, e.g., by an adhesive layer adjacent the encapsulation layer and/or an adhesive layer positioned between the patch 100 and the skin 112.

Figure 35:
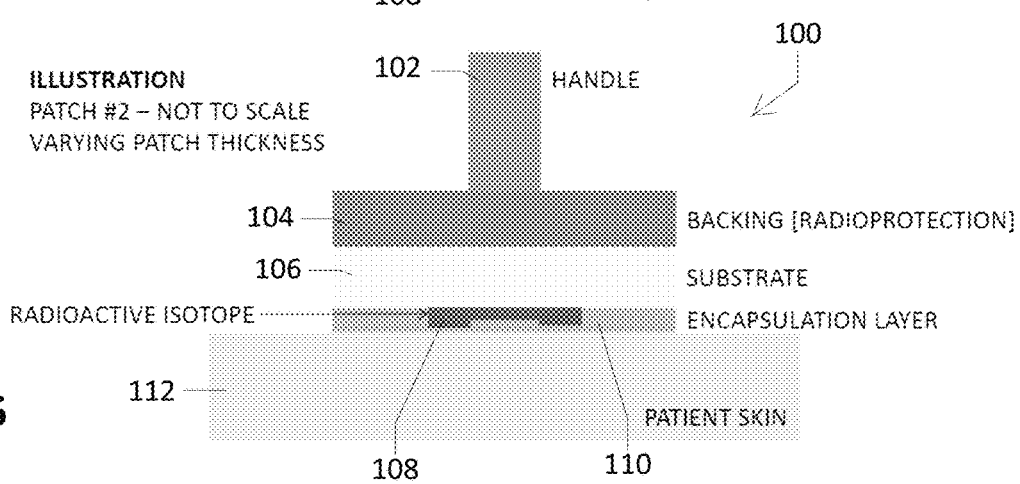
FIG. 35 is a schematic illustration of one embodiment of the disclosed patch positioned against a patient's skin.

FIG. 35 depicts another embodiment of the disclosed skin patch 100, similar to that shown in FIG. 34 and described above. In this embodiment, however, the isotope layer 108 (again activated) comprises a non-uniform thickness. Specifically, as shown, the isotope layer 108 has a center that is thinner than its edges; however, it is also contemplated that the isotope layer 108 may vary in thickness in different areas of the layer 108 (e.g., with one or more thinner portions and one or more thicker portions disposed throughout the layer 108).

Figure 36:
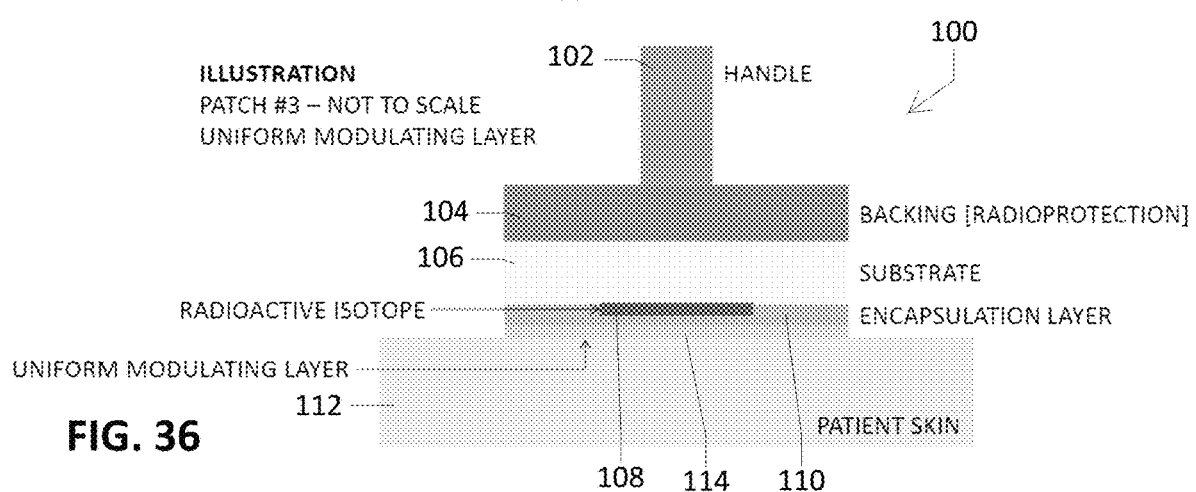
FIG. 36 is a schematic illustration of one embodiment of the disclosed patch positioned against a patient's skin.

FIG. 36 depicts another embodiment of the disclosed skin patch 100, wherein the patch 100 further includes a modulating layer 114 positioned between the encapsulation layer 110 and the patient's skin 112. In this embodiment, the modulating layer 114 is of uniform thickness; however, it is also contemplated that the modulating layer 114 may have varying, non-uniform thickness. As one example, the variation in thickness of the modulating layer 114 may correspond to the variation in thickness of the isotope layer 108 (e.g., the modulating layer 114 may be thinner proximate a thinner section of the isotope layer 108). In the depicted embodiment, the modulating layer 114 is coupled to the encapsulation layer 110, e.g., by an adhesive, and is an integral part of the patch 100; however, it is also contemplated that the modulating layer 114 may, in some embodiments, be applied separately from the patch 100. As shown, the modulating layer 114 is positioned between the encapsulating layer 110 and the patient's skin 112. In this embodiment, the modulating layer 114 is coupled to the patient's skin 112, e.g. by an adhesive.

Figure 37:
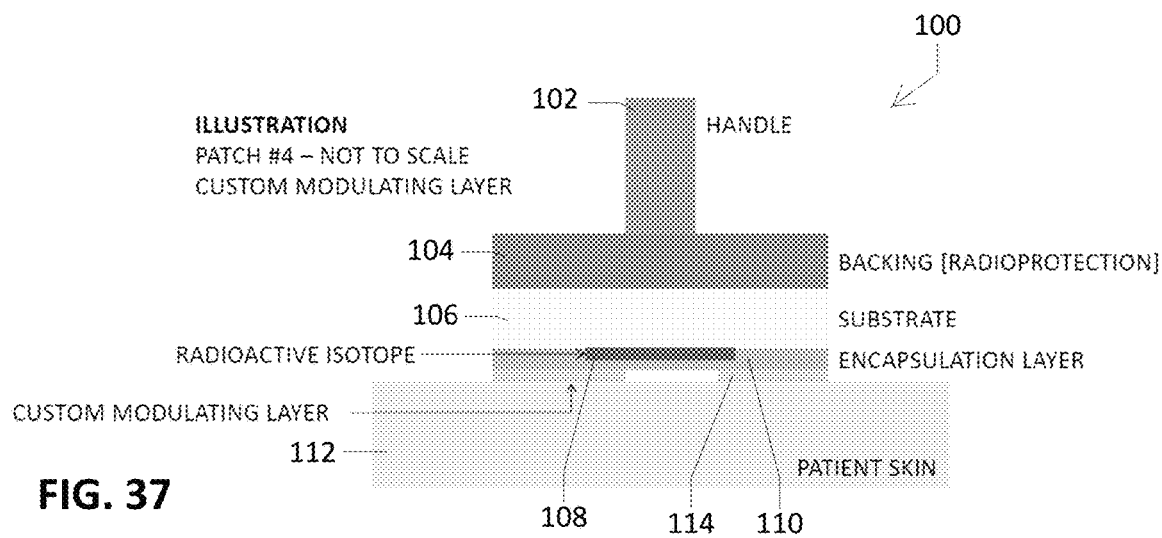
FIG. 37 is a schematic illustration of one embodiment of the disclosed patch positioned against a patient's skin.

The embodiment of FIG. 37, like the embodiment depicted in FIG. 36, includes a modulating layer 114. In this embodiment, the modulation layer 114 is not continuous. Rather, at or near a center of the modulating layer 114, below a portion of the isotope layer 108, there is no modulating layer 114. A non-continuous modulating layer 114 may aid in controlling the amount of radioactive energy delivered at different portions of the patient's skin lesion. While the portion of the modulating layer 114 omitted is shown in a central location of the patch 100, it is also contemplated that the modulating layer 114 may be selectively omitted at different positions along the base of the patch 100 depending on the desired amount of radioactive energy at the different positions.

Figure 38:
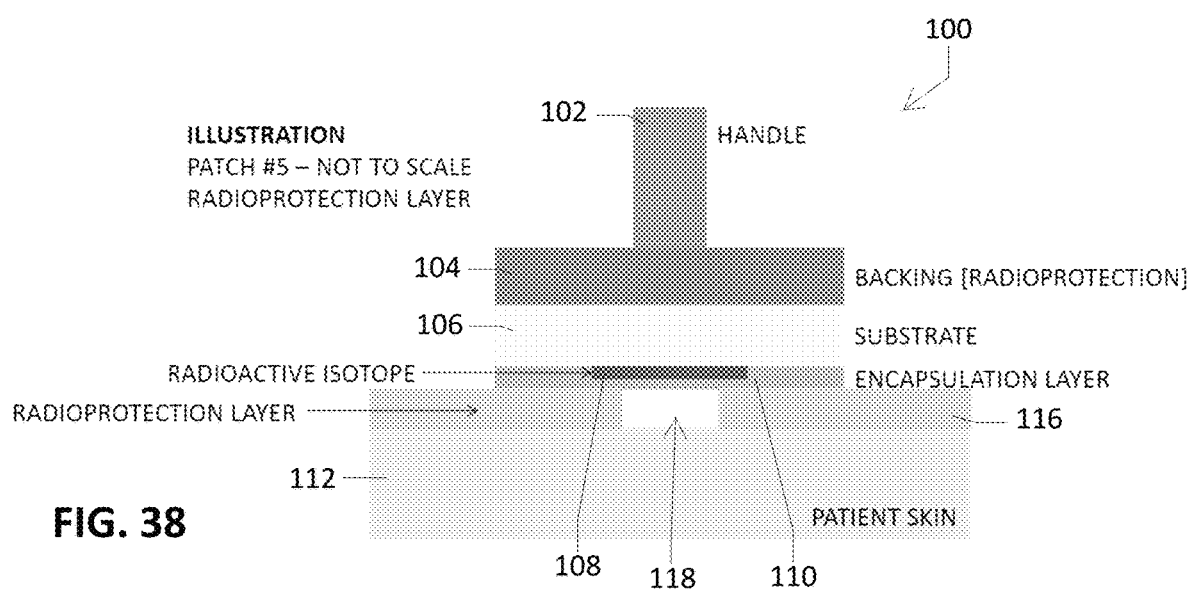
FIG. 38 is a schematic illustration of one embodiment of the disclosed patch positioned against a patient's skin.

FIG. 38 depicts another embodiment of the disclosed skin patch 100, wherein the patch 100 further includes a radioprotective layer 116 positioned between the encapsulation layer 110 and the patient's skin 112. In many embodiments, the radioprotective layer 116 may be a separate structure, that may be coupled to the encapsulation layer 110, e.g., by an adhesive, in other embodiments the radioprotective layer may be combined with a modulating layer and/or may be a separate layer. In the depicted embodiment, the radioprotective layer 116 is longer or wider than the encapsulation layer 110, covering a greater surface area on the patient's skin 112 than the encapsulation layer 110. The radioprotective layer 116 may be coupled to the patient's skin 112, e.g., by adhesive. As one example, the radioprotective layer 116 may be separate from the patch 100 and may be applied to the patient's skin 112 prior to application of the skin patch 100. As another example, the radioprotective layer 116 may be a part of the disclosed patch 100 and may couple the patch 100 to the patient's skin 112.

The radioprotective layer 116 may help to protect the patient's skin 112 around the skin lesion from radioactivity. The radioprotective layer 116 may also allow the practitioner to use a skin patch 100 with an area that is larger than the area of the skin lesion. In many embodiments, the radioprotective layer 116 may be custom sized and shaped to match the size and shape of the patient's skin lesion. In the depicted embodiment, the radioprotective layer 116 defines a gap or hole 118 through the radioprotective layer (i.e., the radioprotective layer 116 is non-continuous) that allows more radiation to pass to the patient's skin 112, e.g., at the site of the lesion; however, it is also contemplated that the radioprotective layer 116 may be thinner (and, wherein the gap or hole is omitted) at the site of the lesion. As shown, the gap or hole 118 may be positioned adjacent or directly beneath the isotope layer 108. In the depicted embodiment, the gap or hole 118 is smaller than the isotope layer 108; however, it is also contemplated that the gap or hole 118 may be the same size as the isotope layer 108. In several embodiments, the radioprotective layer 116 may be positioned on the patient's skin 112 (either as part of the patch 100 or separate from the patch 100) to align the gap or hole 118 with the skin lesion.

EXAMPLES

Example 1: Preliminary Work to Determine Fabrication Method

An initial fabrication method involved vacuum deposition to produce skin patches. With this method, holmium oxide was used with a radio frequency sputtering technique. However, this deposition technique proved to be very slow and impractical for the thickness required to obtain an effective dose. This initial method, however, showed that the 1 MW TRIGA reactor at the Federal Center in Lakewood, CO could activate enough holmium to achieve therapeutic activity ranges provided that the holmium thickness target is achieved.

The patches produced by the initial fabrication method were tested for their emission depth. For example, using simulation software (e.g., VARSKIN4), the penetration of the beta particle into the skin could be modeled. The depth and dose profile of the beta particles emitted from the patch was calculated. It was confirmed that the dose was being applied to a superficial layer of skin with most of the dose deposited in the first few mm of skin (where a tumor would be located). FIG. 3 shows the resulting dose profile assuming a cylindrical source.

Figure 12:
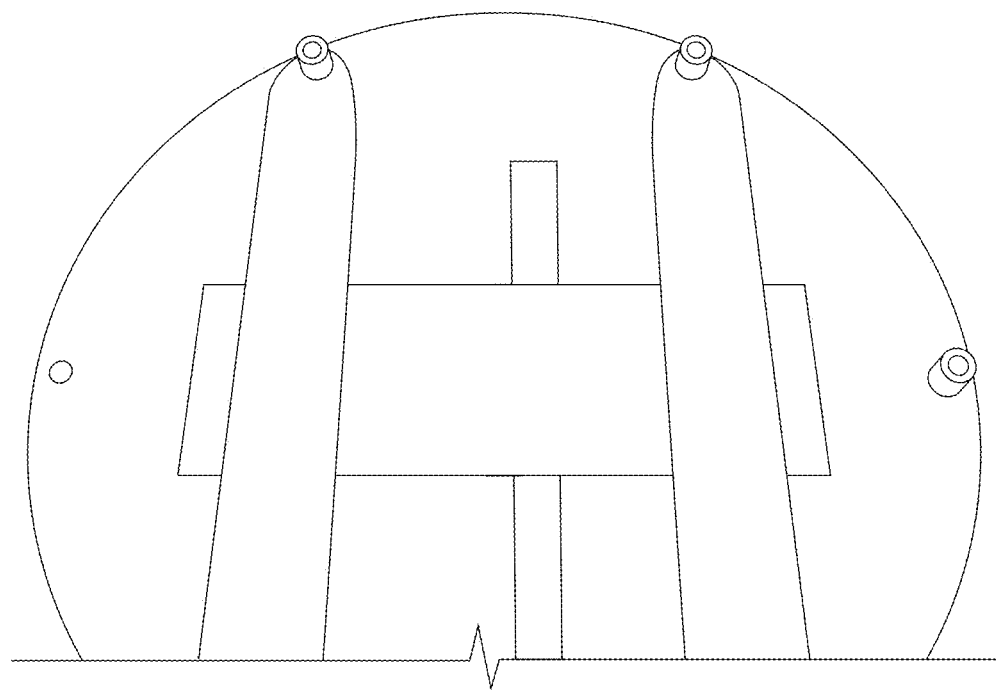
FIG. 12 shows visible flaking on a sample.

Another initial fabrication method used KAPTON tape as the substrate for the skin patch. Pure holmium metal, rather than the oxide, was used, and DC sputtering was applied, which greatly improved the deposition rate. However, the holmium started flaking off of the tape before the target thickness of 2 μm was reached, as seen in FIG. 12. FIG. 12 shows flaking visible in the center of the sample. This flaking means that the sample could not be irradiated because doing so would release radioactive particles and result in unwanted contamination.

To resolve the flaking problem, various types of KAPTON sheet were tested with an aluminum adhesion layer that could be disposed between the tape and the holmium. Ultimately, it was determined that cleaning the KAPTON with solvents such as acetone and isopropanol, then drying with compressed nitrogen prevented most of the flaking.

Example 2: Fabrication method

A piece of KAPTON may be cut to the desired size and any dust may be removed. In the fume hood, the KAPTON may be rinsed off with acetone then with isopropanol, making sure that the sample does not start drying between rinses. The sample may be quickly dried using compressed air, making sure again that the solvents do not evaporate before getting blown off.

The sputtering is in the standby state. The high-vac valve is open, and the cryopump is cold (around 50° K historically). The gate valve (between the main chamber and the loadlock) is closed. The loadlock roughing valve is closed and the foreline is open. The turbopump is running (historical steady state: 75 krpm, 0.19 A) and the turbo gate valve is open. The sputtering power supply is turned off, the MFC valve is closed, the soft vent and vent valves are closed, and the pressure in both the loadlock and the main chamber is in the $1 \times 10^{-6}$ Torr range.

From the standby state, the turbo gate valve is closed and the soft vent valve is opened. The power consumption of the turbo is monitored to ensure that it does not suddenly increase (e.g., indicating that the turbo is being vented as well). The vent valve is opened for the system to reach atmospheric pressure.

The loadlock is opened and the sample holder is removed (for example, the magnet on the transfer arm might need to be rotated out of the "lock" position, with a simple 90 degree rotation). The KAPTON sample is taped onto the sample holder with KAPTON tape, and a little piece of silicon (cleaned the same way as the KAPTON) is also taped onto the sample to estimate the deposited thickness of holmium on the KAPTON sample. The sample holder is loaded back into the loadlock.

The vent valves and foreline valves are closed (such that the turbo is no longer backed by the mechanical pump). The system is not left in this state for extended periods of time. The loadlock roughing valve is opened and the mechanical pump roughs the system to about $1 \times 10^{-2}$ Torr. In many embodiments, lower vacuum values, such as $1 \times 10^{-3}$ Torr (or mTorr) may be used. The roughing valve is closed and the foreline valve is opened. The turbo gate valve is slowly opened to maintain the current reading below 0.25 A to prevent damage to the turbo engine. Once the turbo gate valve is fully open, the system pump is lowered to about $1 \times 10^{-6}$ Torr levels, for example about $0.5 \times 10^{-6}$ Torr to about $5 \times 10^{-6}$ Torr.

The rotating part of the sample holder in the main chamber is set to position 1. The magnet on transfer arm is rotated to "lock" position and the sample holder is transferred from the loadlock to the main chamber. The main chamber is set to position 2, and after the sample holder reaches that position, the transfer arm is unlocked and retracted to the loadlock. The gate valve is closed and the rotation of the sample holder is initiated. The argon gas supply and the regulator output are opened with the output pressure around 5 psi. The argon MFC valve and the toggle MFC controller are opened to the ON position. Time is allowed for the pressure in the system to settle and for MFC controller value to reach equilibrium (around 10-15 usually). The throttle valve and MFC are used to raise the pressure to 10 mTorr (typical MFC values are in the 25-35 range). Note, the throttle valve has two parts: a switch that toggles whether the valve is being opened or closed and a joystick that actually controls the rate at which the throttle valve changes.

After about a minute, the sputter power supply is turned on (with the high voltage cable plugged into the gun to be used). Before the "output" button is selected, the pressure in the system is stabilized and the power set point is 20 W. Power is output to the system and the formation of a plasma is visually verified. The power is slowly increased to 100 W, and the system is allowed to "warm up". The pressure in the chamber sometimes decreases and the MFC can be used to "top off" the pressure. The shutter to the gun to be used is opened (controlled by a knob on the top of the chamber) and sputtering is initiated. Initial settings are recorded (e.g., power, voltage, current, pressure, and MFC value).

After sputtering, the shutter is closed and the final conditions are recorded. Power is slowly ramped down to 20 W, the output button is selected, and the power supply is turned off. The MFC controller is turned off and the throttle valve is opened completely. The system is given time to pump back down to mid $1 \times 10^{-6}$ Torr levels. The sample holder is set to position 1 and the gate valve is opened. The sample holder is transferred to the loadlock and the gate valve is closed. The steps from the standby state discussed above are applied again to vent the loadlock and remove the sample. This process produces patches with a predictable thickness.

Figure 13B:
FIG. 13B shows topographic SEM images at 1400× magnification of a patch after testing.
Figure 13A:
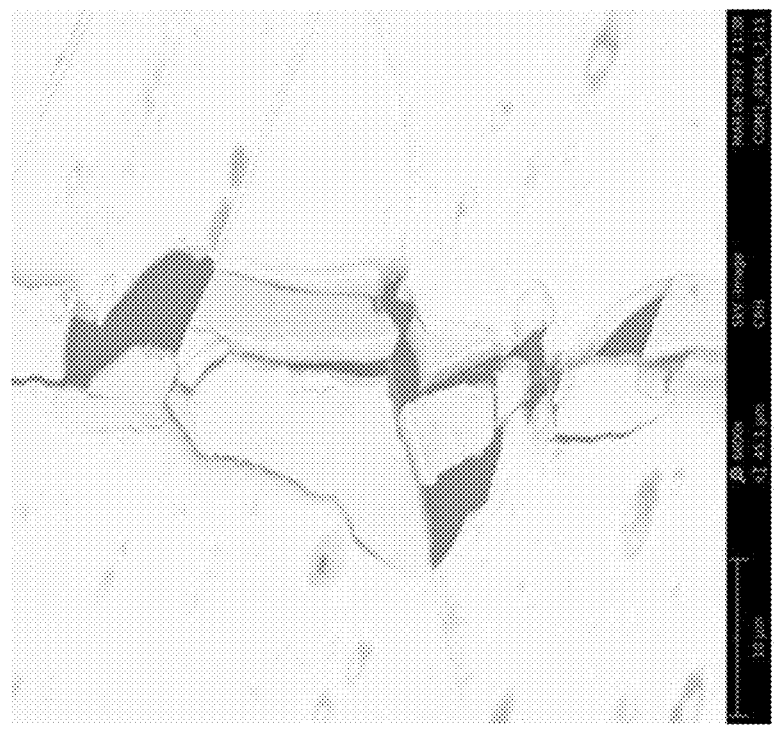
FIG. 13A shows close-up SEM images at 6000× magnification of a patch after testing.
Figure 14:
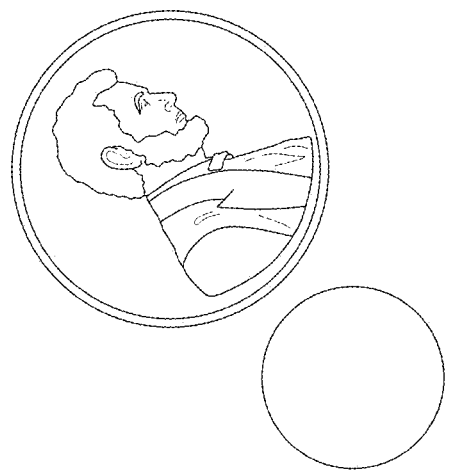
FIG. 14 shows an example of a patch before encapsulation and irradiation.

After the patches are made, it is determined whether the patches need to be encapsulated to prevent flaking caused by applying the patch to a patient. Produced, non-radioactive, patches are stress-tested by repeatedly rolling them up tightly simulating an application to an area of the body with high curvature. All the patches developed cracks after stress testing. FIGS. 13A-13B show SEM images of a patch after testing. FIG. 13A shows a SEM picture of a holmium patch at 6000× magnification, showing a close-up of flaking from cracks in the holmium layer. FIG. 13B shows a SEM picture of a holmium patch at 1400× magnification, showing a topographic view of a holmium layer with visible cracks and missing flakes of holmium along the cracks. To remedy this problem, the patches are covered with a thin layer of KAPTON tape (25 µm) since the additional KAPTON layer has a negligible effect on the delivered dose. This is done by applying the KAPTON like a piece of tape onto the patch and making sure that there are no air bubbles. The encapsulated patches should contain all the radioactive holmium even if it were to crack during the application process. FIG. 14 shows an example of a produced patch before encapsulation and/or irradiation. Some rudimentary measurements were done with the SEM after irradiation to verify the integrity of the encapsulation layer and no visible cracks were found in the KAPTON.

Example 3: Measuring for Uniformity in Thickness

Any non-uniformities in the deposition rate were measured. In one experiment, holmium was deposited on silicon substrates and a profilometer was used to measure the thickness variations both in time and in position on the mask. It was determined that the system had a fairly uniform deposition (less than 5% thickness variations) over a 1 inch radius circle around the center of the mask. In addition to the uniformity of the deposition, the deposition rate itself proved to be large enough to produce patches a few µm in thickness within an hour. These thicknesses provide the patches once irradiated with a high enough activity for therapeutic doses.

Example 4: Investigations into Anomalous Deposition Behaviors

Figure 15A:
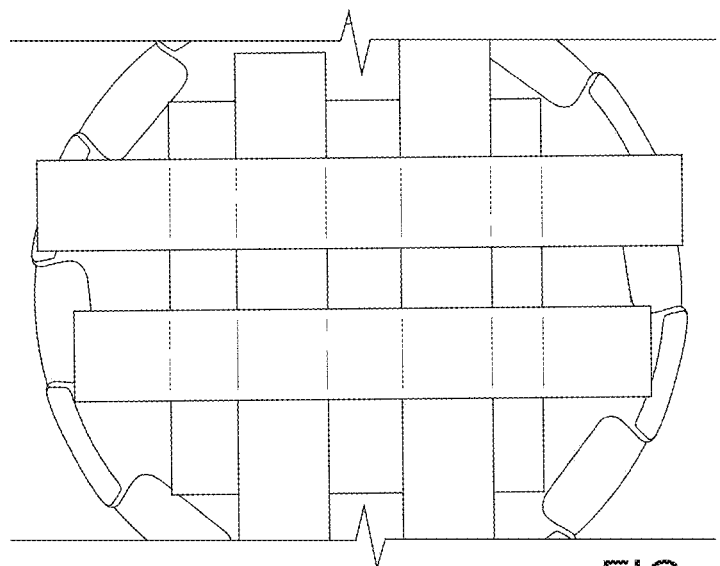
FIG. 15A shows a sample with minimal holmium deposition on a KAPTON substrate.
Figure 15B:
FIG. 15B is a close up view of the sample of FIG. 15A.

Experiments were conducted to produce patches with desired geometries. In one experiment, a tape mask was made into a desired shape; however, this did not allow for production of patches with exactly the same geometry between runs. Instead, while developing a method to produce patches with a specified area, a mask made out of KAPTON was tested. This test showed interesting results where there was no deposition on the KAPTON sample, as shown in FIGS. 15A-15B. FIG. 15A, for example, shows no deposition on the hole cut in the KAPTON mask. A ring feature is faintly visible on the mask and tape around the center has a lower deposition. FIG. 15B shows a close up of the same sample, with the halo around the center more defined. On the other hand, when silicon was used as a substrate, an oxide layer deposited (identified by the multicolored lines on the edges of the deposition). FIG. 9 shows a direct comparison between the deposition on KAPTON and that on silicon. It was determined that what could be causing the decrease in deposition on the KAPTON was an accumulation of charge on the mask (the silicon was doped enough to dissipate any excess charge). The mask was coated with holmium on both sides to create a conducting layer and a graphite sticker was used in scanning electron microscopy (SEM) to ground the mask to the sample holder. This process had no effect and there was still barely any deposition on the KAPTON samples. Instead, the KAPTON tape masks were selected for use with the patches, as they proved to be effective and easy to implement.

Example 5: Measuring Activity of the Patches

Different methods were tested to determine holmium activity with precision and certainty. In one method, the number of holmium atoms in the sample were determined, the activation rate in the reactor from the neutron fluence at the reactor was determined, and the half-life of holmium was converted to a decay rate. The deposition rate and the sputtering time were used to determine the number of targets. Equation 4 shows the relationship between these parameters and the number of targets:

$$N_{Ho} = \frac{RTA\rho_{Ho}N_A}{MW_{Ho}}$$

Where R is the deposition rate, T is the sputtering time, A is the area of the patch, $\rho$ is the density of holmium, $N_A$ is Avogadro's number, and MW is the molecular weight of holmium. However, this method turned out to have a large uncertainty, especially when calculating the area of the patch. Although area measurements were made more precise by using imaging software, a different method was tested. In another method, the samples were weighed before and after deposition to measure the mass of deposited holmium ($m_{Ho}$). Equation 4 above then reduces to Equation 5 below:

$$N_{Ho} = \frac{m_{Ho}N_A}{MW_{Ho}}$$

The activation rate for the sample is determined by the number of holmium targets ($N_{Ho}$), the neutron flux ($\Phi$), and the thermal neutron capture cross section of holmium ($\sigma Ho$), as reflected by the following Equation 6:

$$R_{activation} = N_{Ho}\Phi\sigma_{Ho}$$

By definition, the decay rate is related to the half-life, as shown in the below Equation 7:

$$\lambda = \frac{\ln(2)}{T_{1/2}}$$

Putting all these quantities together, the final activity of the sample can be determined from just holmium, as shown by the below Equation 8:

$$A = R_{activation}\left(1 - e^{-\lambda t_{reactor}}\right)e^{-\lambda t_{cooling}}$$

This calculated activity is in Becquerel (Bq) or decays per second, and to convert to Curies (Ci), the value is divided by $3.7\times10^{10}$ [Bq Ci$^{-1}$].

Example 6: Measuring Impact of Impurities on Patch Activity

Impurities in the sample may change the activity of the patch. For example, the half-life and neutron capture cross section of an impurity may have an impact on the activity of the patch. In particular, a half-life on the order of a day and a very large neutron capture cross section may have a noticeable impact on patch activity.

Impurities in the holmium-165 target sample were identified (in parts per million by weight). Isotopes that could be made by neutron capture from the trace elements were identified. The main focus was on isotopes created from stable versions of the element with a single neutron capture. However, some isotopes that required 2-3 successive captures were also included for good measure. Even if the isotopes were likely to be generated from intermediate states, they were throttled by the production of those states. For each isotope the following data was recorded: the parts per million (PPM) by weight of the element, the natural abundance of the mother isotope, the neutron capture cross section of the mother isotope, the half-life and decay mode, and the half-life of the produced daughter isotope. From this data, a metric, "weighted production" was established, to estimate the impact of each possible isotope on the final activity. This "weighted production" takes into account the natural abundance, the ppm of the element, and the neutron capture cross section. FIG. 16 shows the collected data sorted by weighted production. The "isotopes" column shows the result of an impurity in the target capturing a neutron through (n,γ) reactions. The PPM, capture cross section, and natural abundance are all relative to the initial, stable impurity. The isotopes with a weighted production above 100 were considered to contribute significantly to the activity of the patch.

Other isotopes were considered as significant impurities. For example, three isotopes were tested that were two neutrons removed from a stable element, Ta-183, Dy-166, and Lu-178. These isotopes were included because their neutron capture cross section was very large and their half-life was on the same order of magnitude as holmium. The activity of "holmium impurities" was also tested, such as a metastable state of holmium-166 with a half-life of 1200 years and the possible production of holmium-167 from holmium-166, but these contributions were negligible.

The following Equation 9 was used to calculate the activity of each impurity. The only difference was in the calculation of the number of targets. The impurity content was given in percent weight and converted to molar fraction.

However, since the impurities represent such a small fraction of the overall mass, the weight fraction was adjusted by a ratio of molar masses:

$$\%_{mole} = \%_{weight} \frac{MW_{Ho}}{MW_{impurity}}$$

To get an idea of the activity of the three elements requiring two neutron captures, the number of atoms of the intermediate state were calculated. The activity of an element and the number of nuclei of that element are related as follows in below Equation 10:

$$N_{nuclei} = \frac{A}{\lambda}$$

Where A is the activity and λ is the decay rate of the nucleus. Then Equation 9 could be used to determine the resulting activity.

Figures 17, 18:
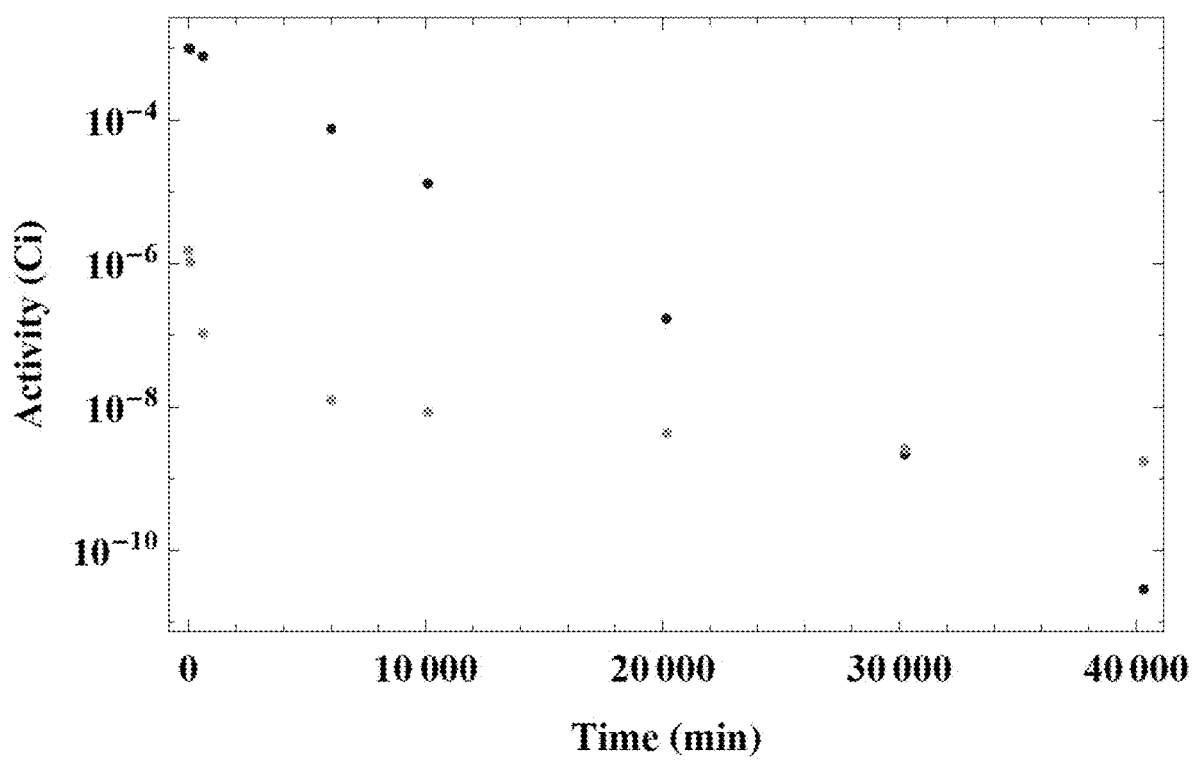
FIG. 17 shows an overview of the radiation produced by and half-lives of isotopes that constitute the main contributors to impurity radiation.
FIG. 18 shows activity versus time of desired holmium-166 activity and activity from impurities in target—blue circles represent activity and the orange circles represent impurities.

To get the final activity, all the activities from the impurities were added to the activity from the holmium. The percent contribution from the impurities was calculated, which provided an indication of the quality of the radiation. It was determined that the activity of the impurities accounted for less than 1% of the total activity of the patch when used. This proportion grew larger as time elapsed due to the long half-life of some of the impurities. However, since these impurities were produced on such a small scale (due to having both a low activation rate and low number of atoms), they do not produce a significant amount of radiation. The main impurities contributing to the activity are $^{165}$Dy, $^{177}$Lu, and $^{66}$Cu. FIG. 17 shows an overview of the radiation produced by these isotopes as well as their half-lives. FIG. 18 shows the activities of holmium-166 and the impurities within starting at 1 mCi and letting it decay over the course of four weeks. As shown, the impurities do not contribute to the activity until the activity has decayed near background levels.

Example 7: Irradiation Process

Various radiation detectors may be used to test for the level of activity of the produced patches. In one experiment, a radiation detector setup was used both from the Colorado School of Mines (herein the "Mines detector") and the USGS facility (herein the "USGS detector"). Both detectors were calibrated. The Mines detector was used for preliminary measurements (low activities) to verify the production process. However, once therapeutic level patches (mCi levels) were produced, the USGS setup was used. The USGS setup allows for much higher activity patches to be measured immediately after their production.

Figure 19:
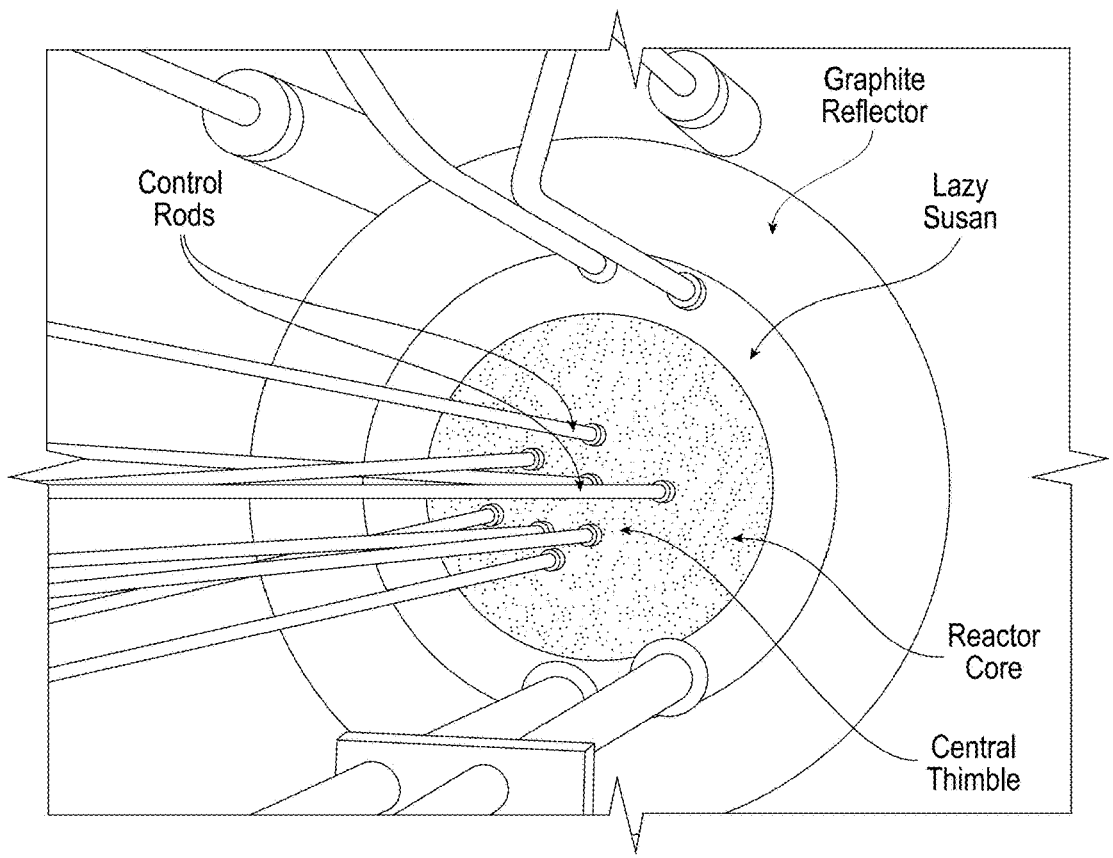
FIG. 19 shows the layout of the USGS reactor.
Figure 20:
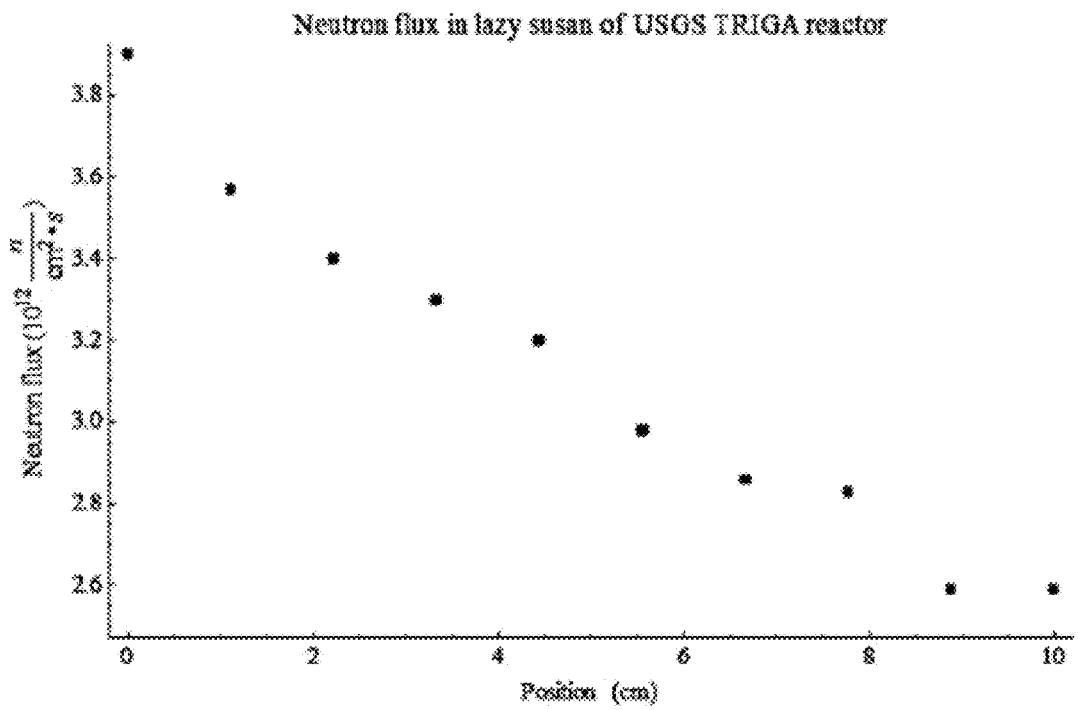
FIG. 20 shows neutron flux as a function of vertical position of a sample in the lazy Susan.

To produce radioactive samples, the $^{165}$Ho patches were activated using the 1 MW TRIGA reactor (operated by the USGS) at the Federal Center. This reactor uses low enriched uranium to generate a large neutron flux in two irradiation locations: the central thimble (wet) and the lazy Susan (dry). FIG. 19 shows the layout of the reactor. The lazy Susan was used for all of the samples because the samples did not need the higher flux from the central thimble and because of higher availability. The neutron flux in the lazy Susan depends on the vertical position of the sample inside of it, as shown in FIG. 20. To obtain accurate measurements of the produced patches, two categories of test runs were conducted: a series of low activity runs using the Mines setup and a few high activity runs using the USGS setup.

Figure 21A:
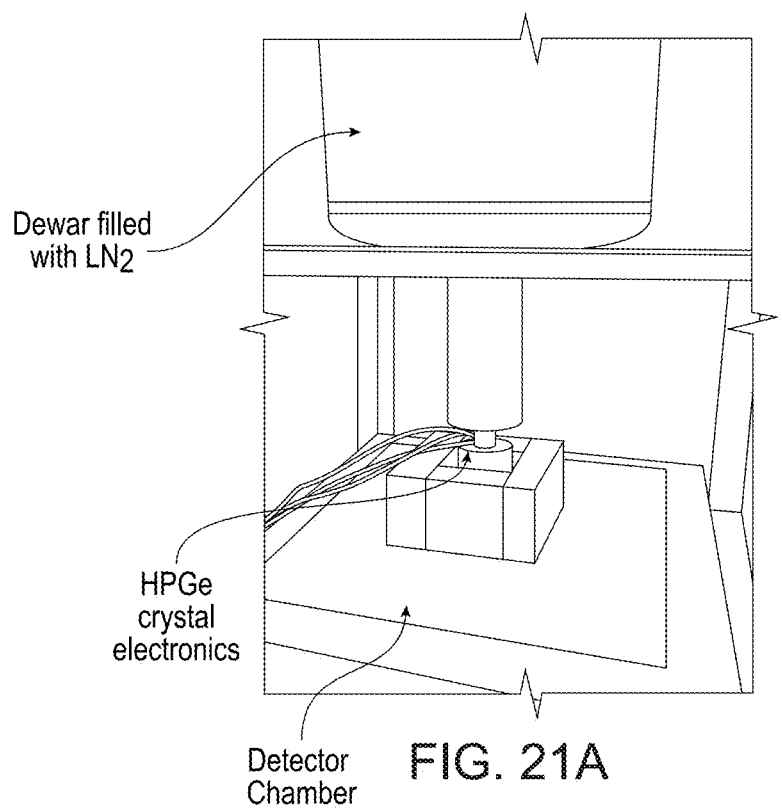
FIG. 21A shows the Mines HPGe detector.
Figure 21B:
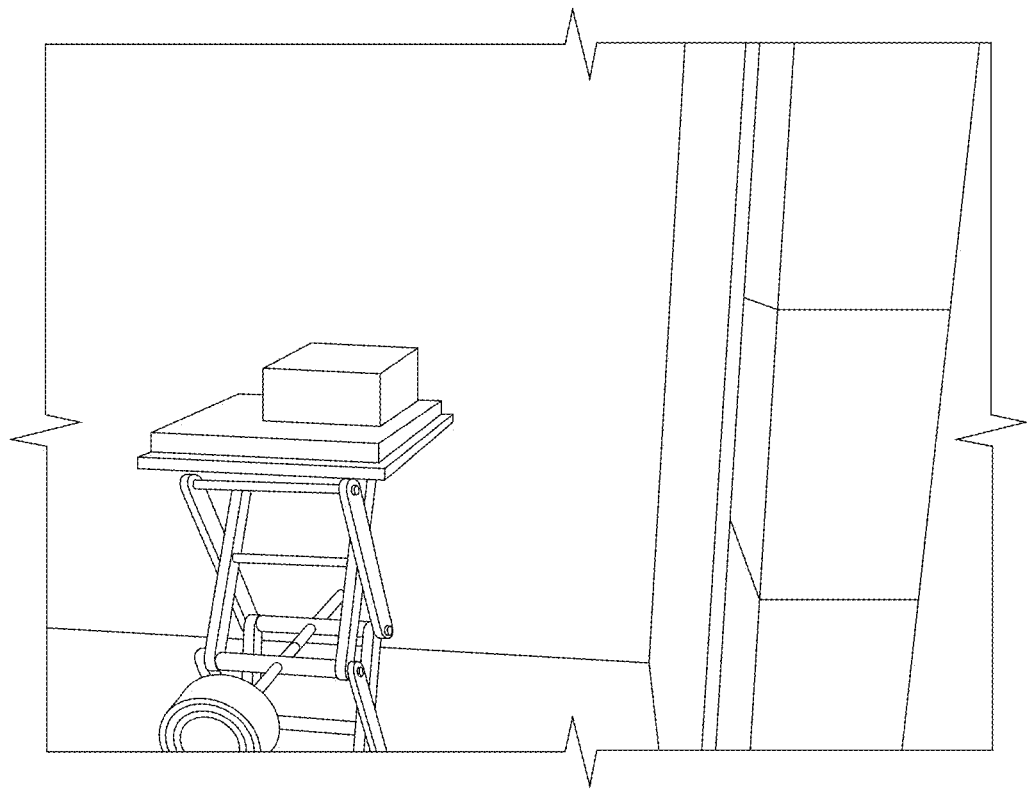
FIG. 21B shows a sample centering system for the Mines detector of FIG. 21A.

The Mines detector is an HPGe (high purity germanium) detector with a 0.5 mm beryllium entrance window. HPGe detectors are used for γ radiation and have a high energy resolution. In addition, the beryllium window prevents air from contaminating the detector without affecting the transmission of low energy γ and X-rays. Such a detector is capable of providing activity measurements since the peak of interest to identify the decay of $^{166}$Ho is at 80 keV, a low energy relative to usual HPGe applications. FIG. 21A shows the detector and FIG. 21B shows the sample centering system. FIG. 21A shows a dewar of the detector filled with liquid nitrogen to maintain the cryogenic temperatures needed to operate the detector. FIG. 21B shows a sample loaded onto the centering device. The lead lined walls provide shielding against background radiation reducing the number of background peaks in the collected spectra.

There are two main efficiencies to consider when using a detector: geometric and intrinsic. The intrinsic efficiency takes into account both defects in the crystal and in the electronics resulting in events hitting the detector but not getting registered. This efficiency is set and there is little one can do to change it. However, the geometric efficiency is a measure of the solid angle coverage of the detector. Assuming an isotropic source, even a detector placed right next to it would only see half of the emitted radiation and therefore have a geometrical efficiency of 50%. This efficiency can be used to decrease the count rate at the detector and avoid deadtime. Deadtime is a measure of detector saturation, if too many γ-rays hit the detector at the same time, the detector will only count some of them as detector response needs time between events to resolve them. Most current detectors have a deadtime estimate which can be used to correct the measured activity but if possible it is preferable to simply minimize deadtime by placing the sample further away. In this example, settings on the geometry of the sample position were not changed since the activities were low enough that the deadtime was well below 5%, allowing for calculation of the absolute efficiency instead which incorporates both intrinsic and geometric efficiencies.

Figures 22, 23:
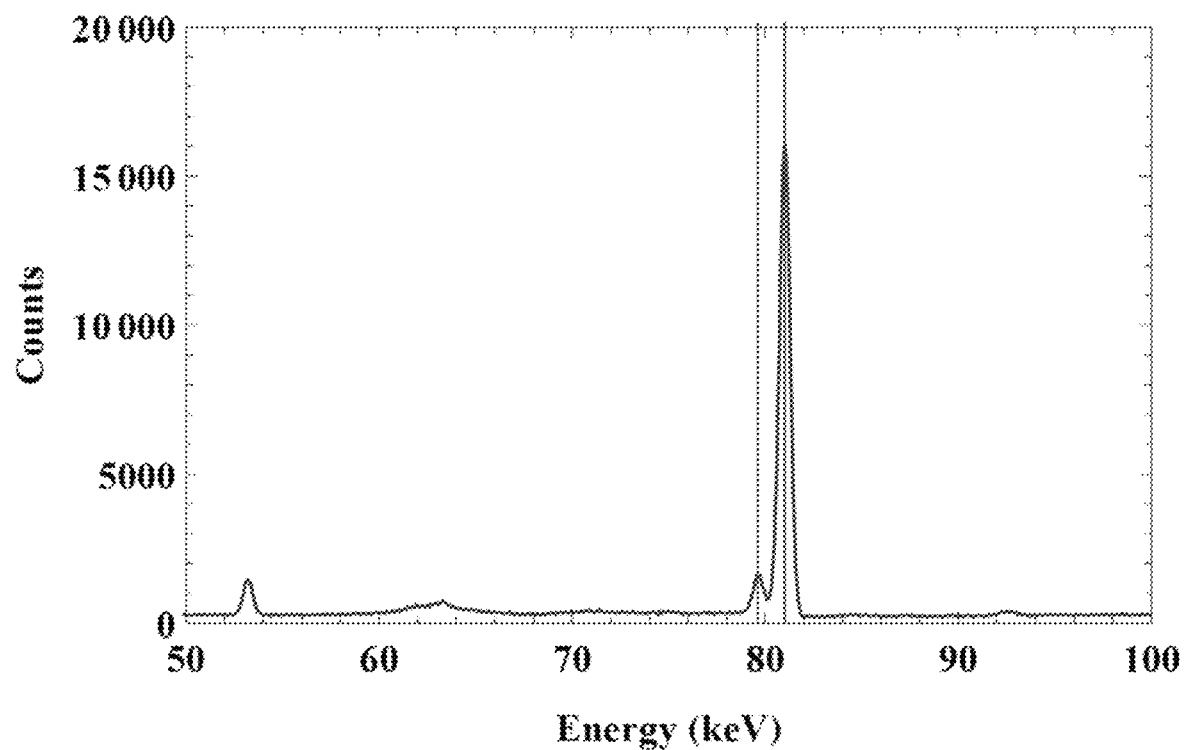
FIG. 22 shows the energies used to calibrate the Mines detector of FIG. 21A.
FIG. 23 shows the spectrum collected with the Mines detector of FIG. 21A.

To calculate absolute efficiency, the detector first needed to be calibrated in order to compare the number of detected events to the expected events. A $^{133}$Ba source as well as a mixed gamma ray source were used to calibrate the detector. FIG. 22 shows the energies used to calibrate the detector with the calibrated number of events adjusted for time elapsed from calibration. The two high energy 60Co lines of the mixed gamma source were not used as they were outside the energy range of the detector. The right half of the table collects the peaks produced by $^{133}$Ba. $^{133}$Ba is an effective calibration source as it has a peak at 80 keV, reducing reliance on the calibration curve and the possible interpolation errors that it generates. However, it was later discovered that $^{133}$Ba actually has two peaks very close to each other around 80 keV. The calibration sheet does not show these as distinct peaks (it only attributes one calibrated count value to the 80 keV region), which means that the calibration was probably done with a high energy detector. After finding the double peak feature in the collected data and not on the calibration datasheet, the NNDC intensity values were used for the 79.6 keV and 81 keV peaks to calculate the expected counts. These peaks are not resolvable by the high energy detector as they are within 2 keV of each other and most high energy detectors have an energy resolution of 2-3 keV full width half max (FWHM). Since the Mines detector is a low energy detector, it has a resolution of better than 1 keV FWHM, allowing the two peaks to be resolved in the barium spectrum. Initially, the efficiency was underestimated as only the second peak was counted. FIG. 23 shows the $^{133}$Ba spectrum collected with the Mines detector. Two peaks around 80 keV (highlighted by the vertical lines) are visible at this resolution. These peaks merge into one shifted peak when the resolution decreases. Data was collected over a few days for both sources to decrease the statistical error in the counts. Efficiency was calculated by integrating over the counts in an energy peak and comparing those to the expected counts. To extract the net counts from the background, a line was fit between the two flat regions on either side of the peak and integrated under it. These counts were considered background and subtracted from the total counts. This method proved to be effective and was compared to the auto fit functionality in RadWare [26] to make sure that the net counts were extracted properly. While RadWare [26] may be used for all the net counts, a Mathematica script was implemented and run over all the spectra.

Equation 11 below shows a common curve used for efficiency calibration. It is composed of a low energy and a high energy component with the low energy curve representing the rapid falloff of efficiency at very low energies (where the energy is no longer high enough for the detector to register a hit reliably).

$$\log(low) = A + B\log\left(\frac{EG}{E1}\right) + C\log\left(\frac{EG}{E1}\right)^2$$

$$\log(high) = D + E\log\left(\frac{EG}{E2}\right) + F\log\left(\frac{EG}{E2}\right)^2$$

$$\mathit{eff}(E_G) = \mathrm{EXP}\left(\left(\log(low)^{-G} + \log(high)^{-G}\right)^{-1/G}\right)$$

Parameters A through G are fit parameters (C is usually set to 0), E1 (100 keV) and E2 (1000 keV) "turn on" the low and high energy portions of the fit, and EG is the energy of the γ-ray.

Figure 24:
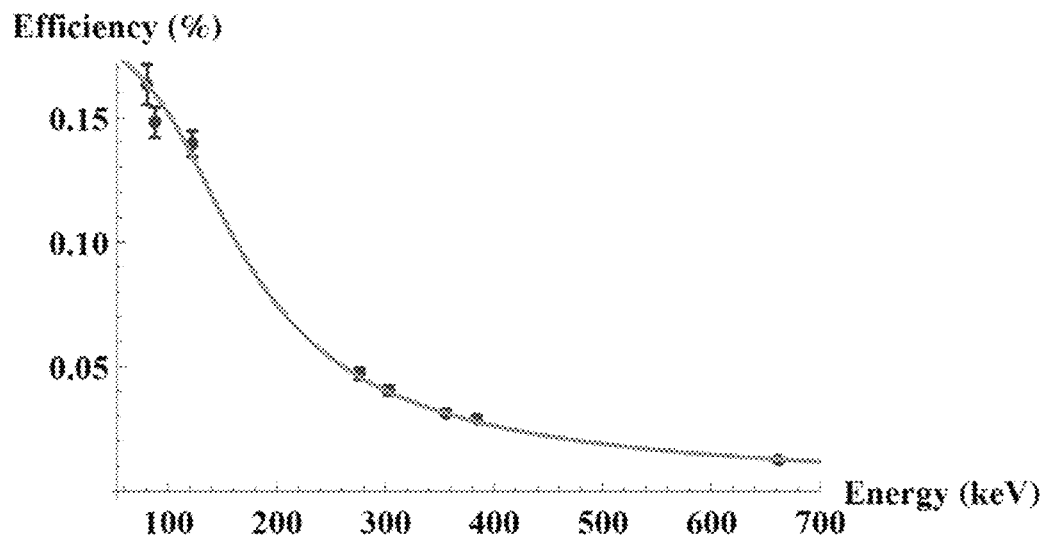
FIG. 24 shows an absolute efficiency curve for the Mines detector of FIG. 21A.

The software RadWare was used to fit this curve to the data and the resulting calibration curve is shown in FIG. 24. As shown, the efficiency reaches a high plateau at 80 keV which is where the peak of interest is for $^{166}$Ho. Once the detector was calibrated, some samples were run and the predicted activity was compared to measured activities.

Figure 25:
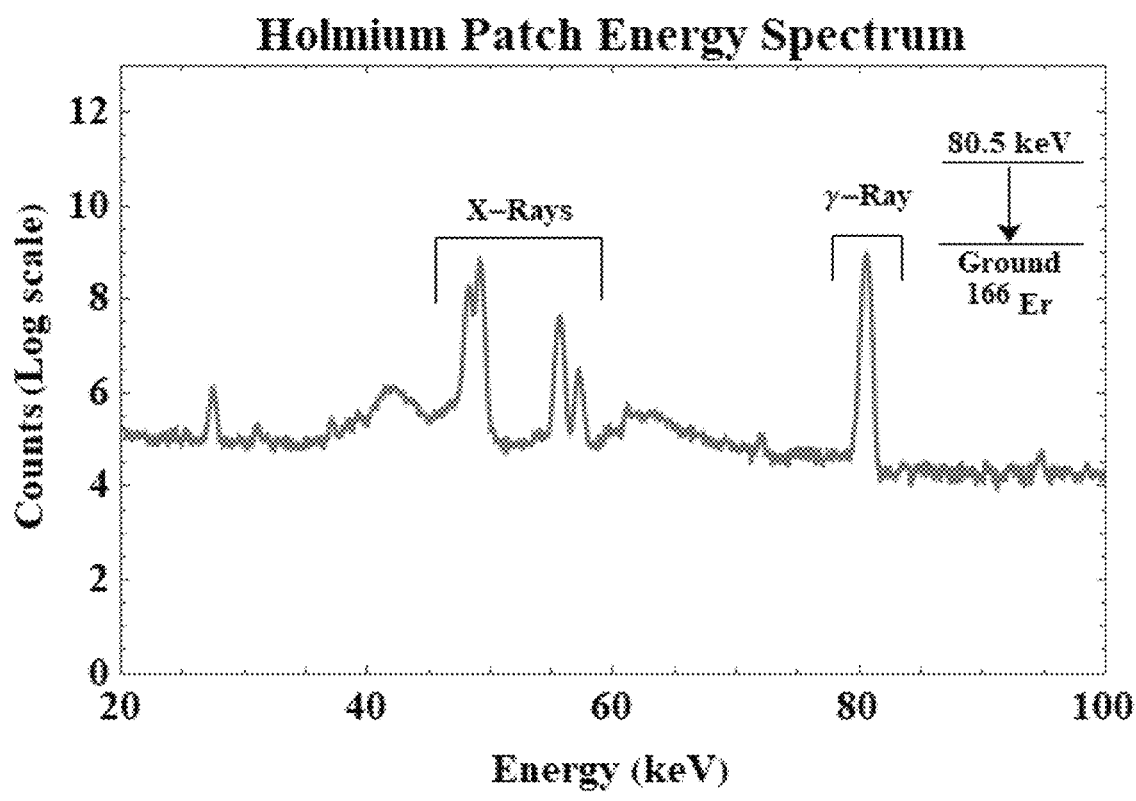
FIG. 25 shows the energy spectrum obtained from the first run of irradiation of a patch of the present disclosure.

In this example, three samples were run for the low activity setup. The first two samples were activated to about 5 μCi to make sure there were no large mistakes in the predictions. FIG. 25 shows the spectrum obtained from the first run with a clear 80.5 keV peak that was used to calculate the total holmium activity using the following Equation 12:

$$A_{Ho} = \frac{N_{Ho}(80.5 \text{ keV})}{\Delta t} \frac{1}{\epsilon * b}$$

where Δt is the duration of the measurement, ε the absolute efficiency, and b is the branching ratio of the 80.5 keV γ-ray. The final run using the Mines detector was a high activity run to mCi levels to test the scaling of the predicted values. Since the sample could not be immediately recovered (due to license restrictions and expected detector deadtime from the high activity), the sample was allowed to decay down to approximately 5 μCi so that all the settings could remain identical. FIG. 26 shows the results of these runs and their predicted activity. The last column in the table shows the results after correcting the efficiency curve using the two barium peaks as described above. Two conclusions can be drawn from the results: a systematic overestimate of the activity of the sample and a large discrepancy in the activity of the last sample. A few possibilities may explain the deviation: shielding from another sample in the reactor decreasing the incoming neutron flux; a lower flux than that used in the predictions; positioning of the sample inside the lazy Susan; and miscalculation of the mass of holmium on the sample.

To try to understand the irradiation process and to continue to develop a patch with a therapeutic activity level (mCi), the USGS detectors were used, as they can handle larger activities (the samples can be placed further from the detector). The USGS setup uses HPGe detectors to assess the activities of the samples. However these detectors are optimized for high energy γ-rays. The USGS detectors have some calibrated positions that are used for highly radioactive samples but these are not designed to be precise, rather, to give an estimate of the activity. FIG. 27B shows the detector setup used with the present example. The two shelves above the detector have V shaped notches in them used to position a can roughly above the detector (for most applications that the USGS deals with, only a rough estimate of the activity is required).

The positioning setup was simple and utilized the top shelf. It consisted of two U shaped brackets with a stopper at the back (a piece of aluminum machined to fit the back of the brackets and prevent the centering devices from sliding through), as shown in FIG. 27A. FIGS. 28A-28B show the holders used to position calibration sources and samples respectively. These slide into the brackets and center the radioactive sample over the detector. The whole setup was centered by eye but the large distance between the setup and the detector meant that small deviations from the "perfect" position would produce insignificant errors in the measured activity. With this setup, samples could be placed in the exact same position and orientation for every run.

Although the source holder worked well, the sample positioning device proved to be impractical. Centering and attaching the sample to the holder while the sample was highly radioactive was difficult, as the tester needed to wear protective equipment. The next iteration for the positioning system was to simply use a plastic sample box. The standard boxes used in the lab fit into the brackets and the dimensions of the samples meant that the sample was naturally centered inside the box.

Figures 29, 30:
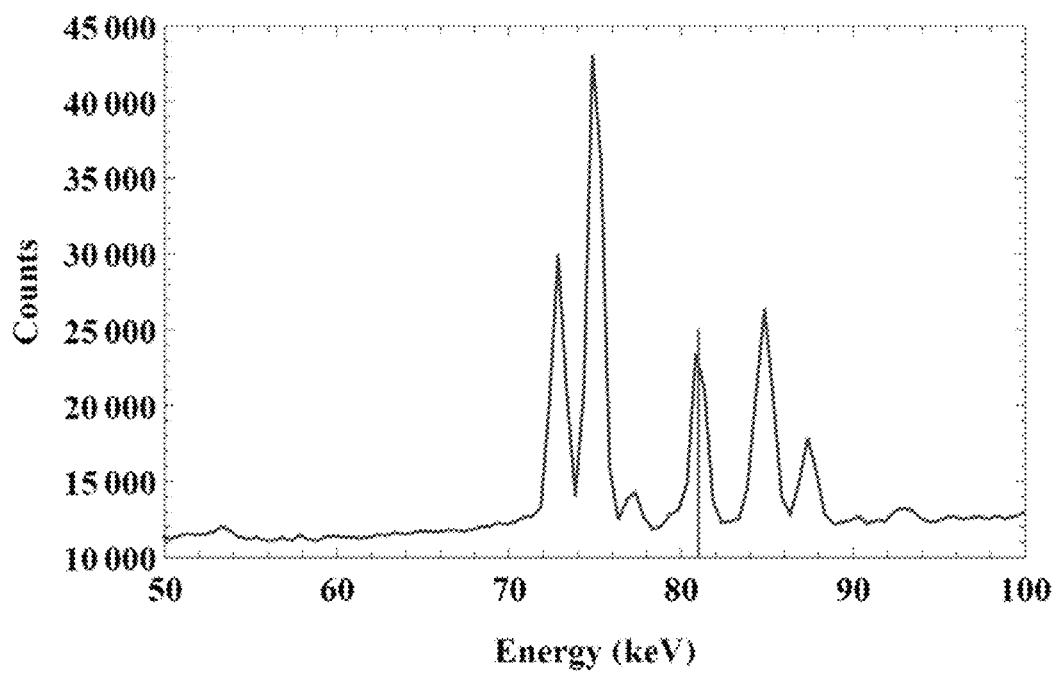
FIG. 29 shows the energies used to calibrate the USGS detector of FIG. 27B.
FIG. 30 shows the $^{133}$Ba spectrum collected with the USGS detector of FIG. 27B.

Just as with the Mines setup, the USGS detector had to be calibrated. A $^{133}$Ba source as well as a $^{152}$Eu source were used to collect data over a large range of energies. The energies used and scaled activities are in FIG. 29. FIG. 30 shows the spectrum collected for the $^{133}$Ba source. As depicted, the detector resolution is worse and there is more background present during the counting. The background is more prominent because there is no shielding around the detector and the data had to be collected for longer periods during the calibration runs. This decrease in resolution removes the double peak that was observed in the spectrum collected in the Mines detector. To calibrate the detector for the large activity samples and keep the dead time low the sources were set far away from the detector, increasing the integration time to achieve good counting statistics with the calibration sources.

FIG. 31 shows the resulting efficiency curve after using Radware to fit the data (the same analysis steps were taken as with the Mines detector and data). For this calibration, an overfitting problem was detected, as there were only two points in the low energy regime. This can be seen in the calibration curve through the first two points. For other applications, this could be a larger issue since the position of the peak is very sensitive to the low energy curve. However, as mentioned previously, interpolation is not necessary from the calibration curve as $^{133}$Ba has a γ-ray energy on top of the ($^{166}$Ho to $^{166}$Er) γ-ray that is of interest. Nevertheless, two more data points were added to the low energy portion of the spectrum by using the X-ray transitions observed in the $^{166}$Ho spectrum. Since the holmium-166 decay has a line on top of a calibrated barium 133 line, the relative detection efficiency for the X-rays can be calculated. The following Equation 13 shows the general process used to add the two data points to the calibration curve:

$$\epsilon(\text{Xray}) = \epsilon(80.5)\frac{N_{Xray}}{N_{80.5}}\frac{b_{80.5}}{b_{Xray}}$$

where Nx denotes the measured counts for a specific energy and bx denotes the branching ratio of that specific photon. This allowed two more points and the calibration curve to be generated, as shown in FIG. 32.

After calibrating the USGS detector, another high activity sample was run. This sample had an activity approximately 25% lower than was calculated (a trend consistent with the other corrected activity measurements performed using the Mines setup). This prompted a reassessment of the fabrication process. The samples were weighed, using an analytical balance, instead of using the area and thickness measurements. The error was determined: holmium was deposited at a lower rate on KAPTON than on silicon. This difference accounted for the systematic error.

To verify the new procedure, two samples were irradiated to high activities (approx. 700 and 1000 μCi respectively), weighed to determine the deposited $^{165}$Ho mass, and measured using the USGS detector. As an additional check, the second sample was allowed to cool to approx. 5 μCi and transferred to the Mines detector setup to be measured there as well. Once the weight of the samples was used to predict the activity instead of thickness, the predictions and measurements agreed within error bars. FIG. 33 shows the final three measurements with their associated predicted activities. The final two samples produced at the USGS had measured activities of 760±42 and 985±54 μCi and predicted activities of 750±35 and 967±35 μCi, respectively. As shown, the data and the prediction lie within error bars of each other, indicating that the described method produces a reliable activity. Additional experiments have produced activity of about 0.73±0.038 mCi.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

The invention claimed is:

1. A skin patch device for treating a skin condition in a patient comprising:
    a substrate layer comprising a substrate material selected for temperature and radiation resistance in an irradiation process;
    a foil layer of metal disposed on an area of the substrate layer, comprising an isotope of an element selected from lanthanum, cerium, praseodymium, neodymium, promethium, samarium, europium, gadolinium, terbium, dysprosium, holmium, erbium, thulium, ytterbium, and lutetium or yttrium,
    wherein the foil layer is configured for activation with a neutron flux in the irradiation process to convert the isotope to a radioisotope that emits beta particles during decay, and
    wherein the foil layer has a spatially uniform thickness that varies by less than 10% over the area of the foil layer disposed on the substrate layer; and
    an encapsulation layer comprising an encapsulation material disposed over the foil layer, wherein the encapsulation material is selected based on temperature and radiation resistance, in the radiation process.

2. The skin patch device of claim 1, wherein the foil layer comprises a holmium 165 or yttrium 89 metal isotope.

3. The skin patch device of claim 1, wherein the substrate material is selected from a polyimide, a polyimide film comprising (4,4'-oxydiphenylene-pyromellitimide), a polymer, a plastic, a metal, or any combination thereof.

4. The skin patch device of claim 1, wherein the substrate layer has a thickness of 0.0125 mm to 0.125 mm, or 0.025 mm to 0.05 mm.

5. The skin patch device of claim 1, wherein the foil layer is deposited on the substrate layer, and positioned between the substrate layer and the encapsulation layer.

6. The skin patch device of claim 5, wherein the encapsulation layer is or comprises a self-adhesive layer or tape layer.

7. The skin patch device of claim 1, wherein the foil layer has a thickness between 10 μm and 250 μm, 25 μm and 125 μm, or 0.1 μm and 10 μm; or, wherein the thickness varies by less than 5% over the area of the foil layer, or by less than 2% over the area of the foil layer.

8. The skin patch device of claim 1, wherein the skin patch device further comprises a backing layer or handle adjacent the substrate layer, wherein the backing layer or handle is configured to absorb radiation from the foil layer.

9. The skin patch device of claim 1, further comprising a modulation layer positioned on an outside surface of the skin patch device, wherein the modulation layer comprises a modulating material that is selected to stop or absorb some or all radiation energy from the foil layer.

10. A method of manufacturing an irradiated skin patch device comprising obtaining a skin patch device according to claim 1, and activating the skin patch device in said irradiation process, with a neutron source adapted to generate the neutron flux.

11. The skin patch device of claim 1, wherein the foil layer comprises a thin film of said isotope deposited on the substrate layer, or a pre-formed or rolled foil of said isotope disposed on the substrate layer.

12. The skin patch device of claim 1, comprising at least a second foil layer of said isotope disposed between the substrate layer and the encapsulation layer, wherein the second foil layer has a same or different thickness selected to modulate a radiation dose delivered to the patient upon application of the skin patch device to treat the skin condition, after said activation in the irradiation process.

13. A method of manufacturing a skin patch device for treating a skin condition in a patient, the method comprising:
preparing a substrate layer from a substrate material selected for temperature and radiation resistance in an irradiation process;
depositing at least one foil layer comprising holmium 165 or yttrium 89 metal on an area of the substrate material to create a holmium or yttrium isotope foil layer having a spatially uniform thickness that varies by less than 10% over the area of the holmium or yttrium isotope foil layer deposited on the substrate material, and configured for activation with a neutron flux in the irradiation process to convert the holmium or yttrium isotope of the foil layer to a radioisotope that emits beta particles during decay; and
adding an encapsulating material selected for temperature and radiation resistance in the irradiation process over the holmium or yttrium isotope foil layer, to create an encapsulating layer thereon.

14. The method of claim 13, wherein the substrate material is selected from polyimide film comprising (4,4'-oxydiphenylene-pyromellitimide), a polyamide, a polymer, a plastic, a metal, or any combination thereof.

15. The method of claim 13, wherein the substrate material has a thickness of 0.0125 mm to 0.125 mm, or 0.025 mm to 0.05 mm.

16. The method of claim 13, wherein the encapsulation material of the encapsulation layer comprises plastic, a polymer, polyimide, a material derived from a poly(p-xylene), a material derived from a variant of poly(p-xylxylene), or any combination thereof.

17. The method of claim 13, wherein the holmium or yttrium isotope foil layer has a thickness between 10 μm and 250 μm, 25 μm and 125 μm, or 0.1 μm and 10 μm; or, wherein the thickness varies by less than 5% over the area of the holmium or yttrium isotope foil layer, or by less than 2% over the area of the holmium or yttrium isotope foil layer.

18. The method of claim 13, further comprising attaching a detachable backing layer or handle adjacent the substrate layer, wherein the detachable backing layer or handle is configured to absorb radiation from the holmium or yttrium isotope foil layer and to protect a practitioner from said radiation when applying the skin patch device to a patient, after said activation in the irradiation process.

19. The method of claim 13, further comprising attaching or depositing a modulation layer adjacent the substrate material, wherein the modulation layer comprises a modulating material that is configured to absorb or stop some or all radiation energy from the holmium or yttrium isotope foil layer, after said activation in the irradiation process.

20. The method of claim 13, further comprising activating the skin patch device in the irradiation process with a neutron source adapted to generate the neutron flux to convert the holmium 165 or yttrium 89 metal to holmium 166 or yttrium 90 metal, respectively.

21. The method of claim 13, wherein depositing at least one foil layer comprises depositing a thin film of said holmium 165 or yttrium 89 metal on the substrate layer by sputtering or physical or chemical deposition, or disposing a pre-formed or rolled foil or sheet of said holmium 165 or yttrium 89 metal on the substrate layer.

22. The method of claim 13, further comprising depositing at least a second foil layer of said holmium 165 or yttrium 89 metal between the substrate layer and the encapsulating layer, with a thickness selected to modulate a radiation dose delivered to the patient upon application of the skin patch device to treat the skin condition, after said activation in the irradiation process.

23. A skin patch device for treating a skin condition in a patient, comprising:
a substrate layer comprising a polyimide substrate material selected for temperature and radiation resistance in an irradiation process;
an encapsulation layer comprising an encapsulating material selected for temperature and radiation resistance in the irradiation process;
an isotope layer comprising a holmium 165 or yttrium 89 isotope metal foil, positioned over an area between the substrate layer and the encapsulation layer,
wherein the isotope layer is configured for activation with a neutron flux in the irradiation process to convert the holmium or yttrium isotope to a radioisotope that emits beta particles during decay, and
wherein the isotope layer has a spatially uniform thickness of between 0.1 μm and 250 μm that varies by less than 10% over the area of the isotope layer between the substrate layer and the encapsulation layer; and
a backing layer adjacent the substrate layer, wherein the backing layer comprises a backing material that is selected to block radiation from the holmium or yttrium isotope foil layer, after said activation in the irradiation process.

24. The skin patch device of claim 23, further comprising a modulation layer and/or radioprotective layer configured to be positioned between the patch and a patient's skin when applied thereto, wherein the modulation layer and/or radioprotective layer are configured to absorb or stop some or all radiation energy from the isotope layer, after said activation in the irradiation process.

25. The skin patch device of claim 23, wherein the isotope layer comprises a thin film of said holmium 165 or yttrium 89 isotope deposited on the substrate layer, or a pre-formed or rolled foil or sheet of said holmium 165 or yttrium 89 isotope disposed on the substrate layer.

26. The skin patch device of claim 23, further comprising at least a second layer of said holmium 165 or yttrium 89 isotope metal foil positioned between the substrate layer and the encapsulation layer, with a thickness selected to modulate a radiation dose delivered to patient upon application of the skin patch device to treat the skin condition, after said activation in the irradiation process.

\* \* \* \* \*

UNITED STATES PATENT AND TRADEMARK OFFICE
CERTIFICATE OF CORRECTION

PATENT NO. : 12,285,627 B2
APPLICATION NO. : 16/657717
DATED : April 29, 2025
INVENTOR(S) : Frédéric Sarazin et al.

Page 1 of 1

It is certified that error appears in the above-identified patent and that said Letters Patent is hereby corrected as shown below:

In the Claims

In Column 31, Claim 16, Lines 31-32 delete "poly(p-xylene)" and replace with --poly(p-xylylene)--

In Column 31, Claim 16, Lines 32-33 delete "poly(p-xylxylene)" and replace with --poly(p-xylylene)--

Signed and Sealed this
Twenty-seventh Day of May, 2025

Coke Morgan Stewart
*Acting Director of the United States Patent and Trademark Office*